(12) United States Patent
Burkett et al.

(10) Patent No.: US 10,709,385 B2
(45) Date of Patent: Jul. 14, 2020

(54) SIDE-LOADING CONNECTORS FOR USE WITH INTRAVASCULAR DEVICES AND ASSOCIATED SYSTEMS AND METHODS

(71) Applicant: Volcano Corporation, San Diego, CA (US)

(72) Inventors: David H. Burkett, Temecula, CA (US); Mark Richardson, Escondido, CA (US); Joseph Burnett, Carlsbad, CA (US)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 558 days.

(21) Appl. No.: 15/374,312

(22) Filed: Dec. 9, 2016

(65) Prior Publication Data

US 2017/0086745 A1   Mar. 30, 2017

Related U.S. Application Data

(63) Continuation of application No. 13/930,787, filed on Jun. 28, 2013, now abandoned.
(Continued)

(51) Int. Cl.
*A61B 5/00* (2006.01)
*A61M 25/09* (2006.01)
(Continued)

(52) U.S. Cl.
CPC .......... *A61B 5/6851* (2013.01); *A61B 5/0066* (2013.01); *A61B 5/0215* (2013.01);
(Continued)

(58) Field of Classification Search
CPC .... A61B 5/0215; A61B 5/6851; A61M 25/09; A61M 2025/09183
See application file for complete search history.

(56) References Cited

U.S. PATENT DOCUMENTS

| 3,649,954 A | * | 3/1972 | Kurtz | H01R 11/22 24/502 |
|---|---|---|---|---|
| 4,651,751 A | | 3/1987 | Swendson et al. | |

(Continued)

FOREIGN PATENT DOCUMENTS

JP    2009202030 A    9/2009

OTHER PUBLICATIONS

International Search Report and Written Opinion received in Patent Cooperation Treaty Application No. PCT/US2013/048546, dated Oct. 7, 2013, 12 pages.

*Primary Examiner* — Max F Hindenburg

(57) ABSTRACT

Intravascular devices, systems, and methods are disclosed. In some embodiments, side-loading electrical connectors for use with intravascular devices are provided. The side-loading electrical connector has at least one electrical contact configured to interface with an electrical connector of the intravascular device. A first connection piece of the side-loading electrical connector is movable relative to a second connection piece between an open position and a closed position, wherein in the open position an elongated opening is formed between the first and second connection pieces to facilitate insertion of the electrical connector between the first and second connection pieces in a direction transverse to a longitudinal axis of the intravascular device and wherein in the closed position the at least one electrical contact is electrically coupled to the at least one electrical connector received between the first and second connection pieces.

23 Claims, 34 Drawing Sheets

Related U.S. Application Data

(60) Provisional application No. 61/665,706, filed on Jun. 28, 2012.

(51) Int. Cl.
*A61B 5/0215* (2006.01)
*A61B 8/08* (2006.01)

(52) U.S. Cl.
CPC .......... *A61B 8/0891* (2013.01); *A61M 25/09* (2013.01); *A61B 2562/227* (2013.01); *A61M 2025/09183* (2013.01); *Y10T 29/49117* (2015.01)

(56) References Cited

U.S. PATENT DOCUMENTS

| | | | |
|---|---|---|---|
| 5,517,989 A | 5/1996 | Frisbie et al. | |
| 5,967,978 A | 10/1999 | Littmann et al. | |
| 6,112,598 A | 9/2000 | Tenerz | |
| 6,142,958 A | 11/2000 | Hammarstrom | |
| 6,544,078 B2 * | 4/2003 | Palmisano | G01R 1/06788 439/762 |
| 7,532,920 B1 | 5/2009 | Ainsworth et al. | |
| 8,692,559 B2 * | 4/2014 | Jin | H01R 11/24 324/538 |
| 9,949,647 B2 * | 4/2018 | Smith | A61B 5/0215 |
| 2002/0146503 A1 | 10/2002 | Burkett et al. | |
| 2003/0028128 A1 | 2/2003 | Tenerz | |
| 2006/0009817 A1 | 1/2006 | Tulkki | |
| 2006/0241505 A1 | 10/2006 | Ahmed et al. | |
| 2008/0300530 A1 | 12/2008 | Massengale | |
| 2011/0160824 A1 | 6/2011 | Ware et al. | |

* cited by examiner

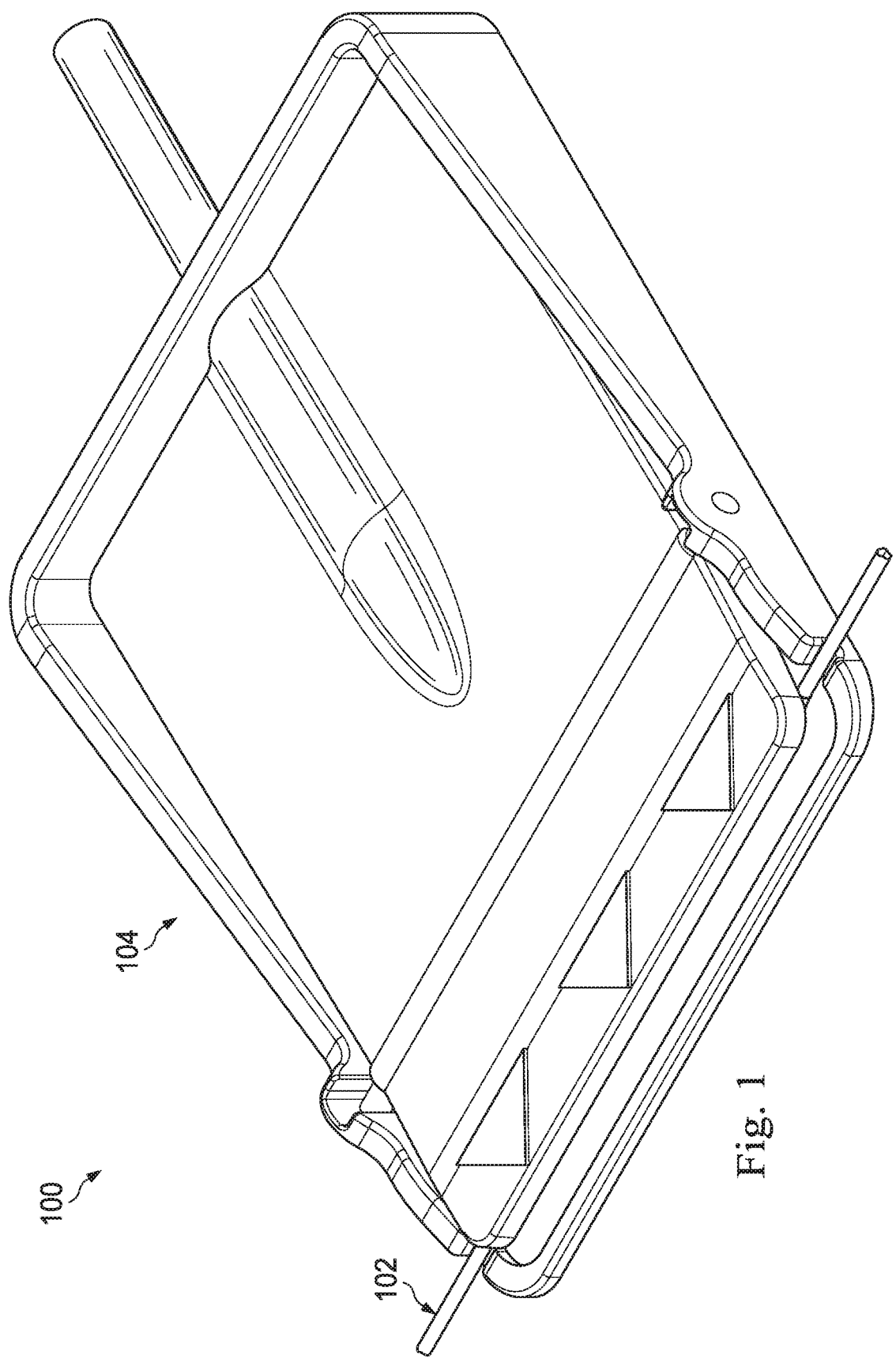

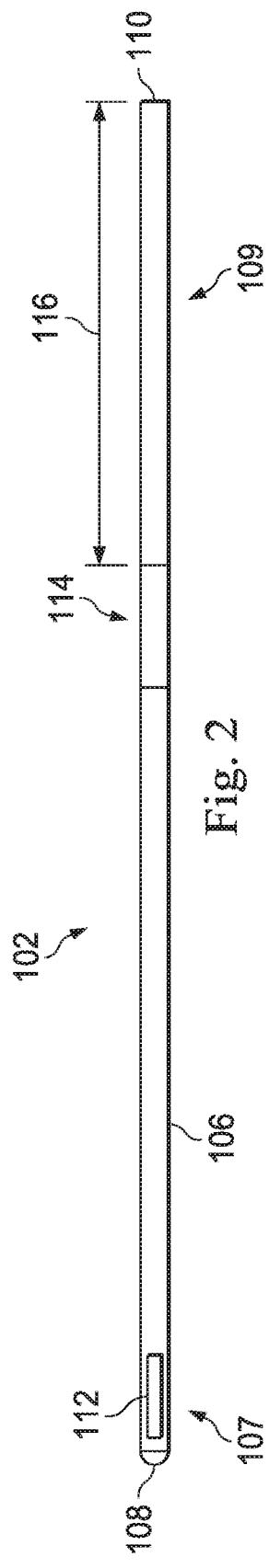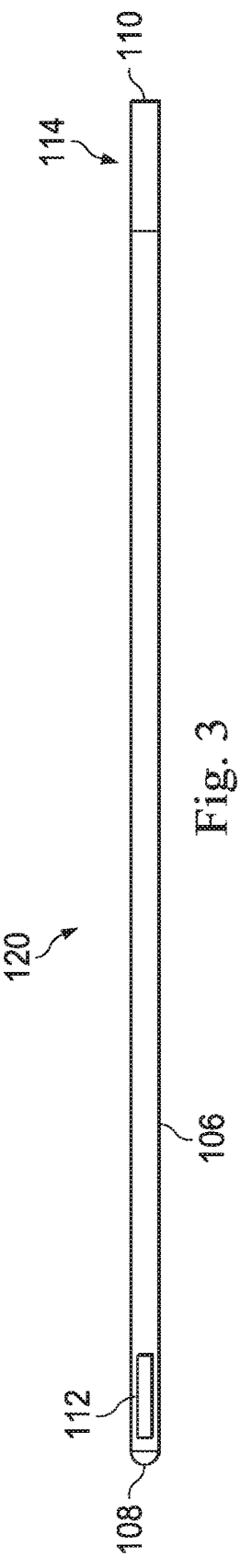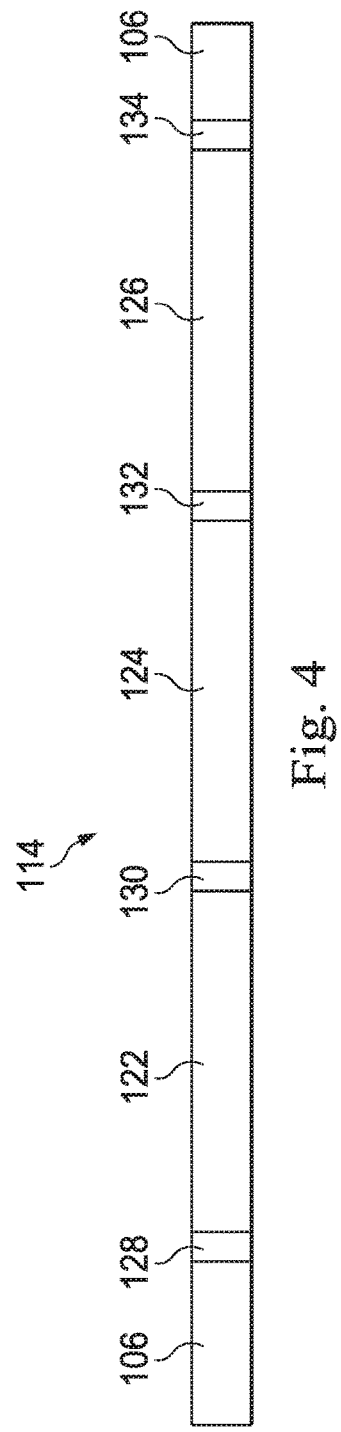

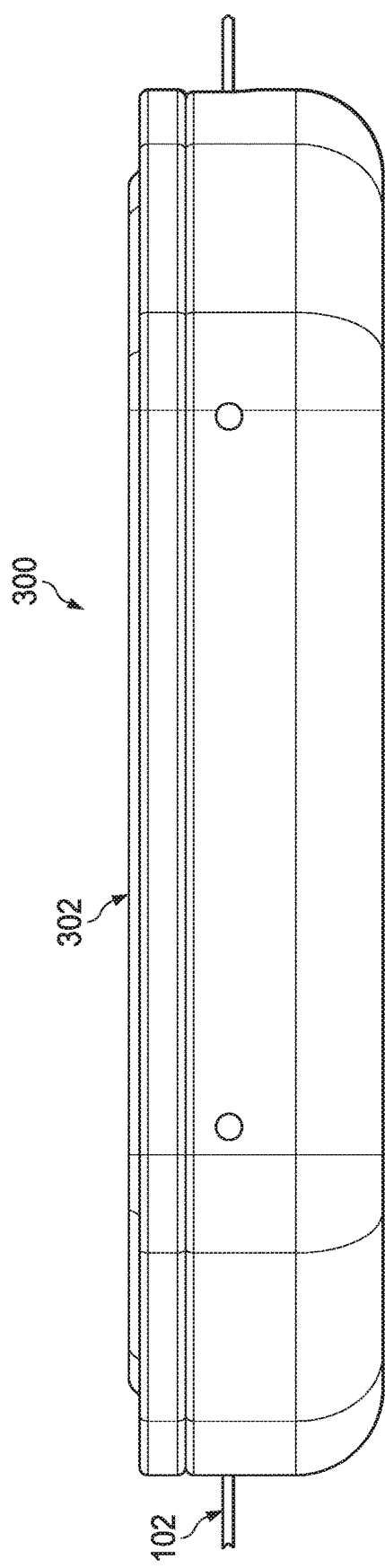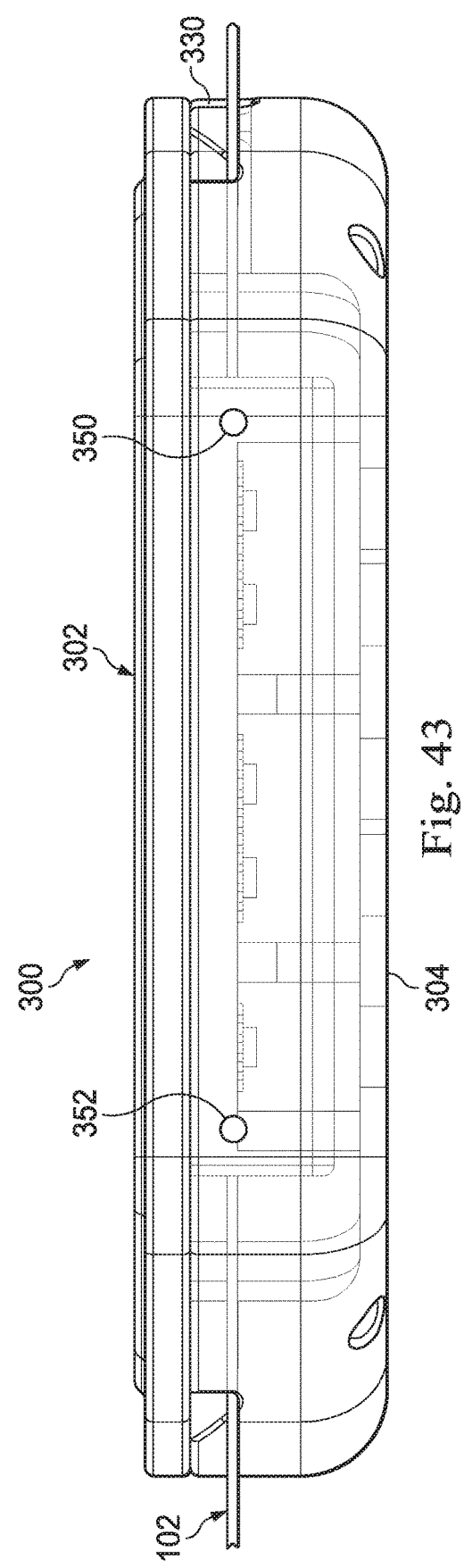

SIDE-LOADING CONNECTORS FOR USE WITH INTRAVASCULAR DEVICES AND ASSOCIATED SYSTEMS AND METHODS

CROSS REFERENCE TO RELATED APPLICATIONS

The present application is a continuation of U.S. Non-Provisional patent application Ser. No. 13/930,787, filed Jun. 28, 2013, which claims priority to and the benefit of U.S. Provisional Patent Application No. 61/665,706, filed Jun. 28, 2012, each of which is hereby incorporated by reference herein in its entirety.

TECHNICAL FIELD

The present disclosure relates to intravascular devices, systems, and methods. In some embodiments, the intravascular devices are guidewires that include one or more electronic components.

BACKGROUND

Heart disease is very serious and often requires emergency operations to save lives. A main cause of heart disease is the accumulation of plaque inside the blood vessels, which eventually occludes the blood vessels. Common treatment options available to open up the occluded vessel include balloon angioplasty, rotational atherectomy, and intravascular stents. Traditionally, surgeons have relied on X-ray fluoroscopic images that are planar images showing the external shape of the silhouette of the lumen of blood vessels to guide treatment. Unfortunately, with X-ray fluoroscopic images, there is a great deal of uncertainty about the exact extent and orientation of the stenosis responsible for the occlusion, making it difficult to find the exact location of the stenosis. In addition, though it is known that restenosis can occur at the same place, it is difficult to check the condition inside the vessels after surgery with X-ray.

A currently accepted technique for assessing the severity of a stenosis in a blood vessel, including ischemia causing lesions, is fractional flow reserve (FFR). FFR is a calculation of the ratio of a distal pressure measurement (taken on the distal side of the stenosis) relative to a proximal pressure measurement (taken on the proximal side of the stenosis). FFR provides an index of stenosis severity that allows determination as to whether the blockage limits blood flow within the vessel to an extent that treatment is required. The normal value of FFR in a healthy vessel is 1.00, while values less than about 0.80 are generally deemed significant and require treatment.

Often intravascular catheters and guidewires are utilized to measure the pressure within the blood vessel. To date, guidewires containing pressure sensors or other electronic components have suffered from reduced performance characteristics compared to standard guidewires that do not contain electronic components. For example, the handling performance of previous guidewires containing electronic components have been hampered, in some instances, by the limited space available for the core wire after accounting for the space needed for the conductors or communication lines of the electronic component(s), the stiffness of the rigid housing containing the electronic component(s), and/or other limitations associated with providing the functionality of the electronic components in the limited space available within a guidewire. Further, due to its small diameter, in many instances the proximal connector portion of the guidewire (i.e., the connector(s) that facilitate communication between the electronic component(s) of the guidewire and an associated controller or processor) is fragile and prone to kinking, which destroys the functionality of the guidewire. Further still, many physicians complain about an inability to reestablish a good connection between the proximal connector and the guidewire even when the guidewire remains fully functional. For these reasons, surgeons are reluctant to remove the proximal connector from the guidewire during a procedure for fear of breaking the guidewire or not having a good connection when reattaching the proximal connector. However, having the guidewire coupled to the proximal connector further limits the maneuverability and handling of the guidewire.

Accordingly, there remains a need for improved connectors for use with intravascular devices (e.g., catheters and guidewires) that include one or more electronic components.

SUMMARY

Embodiments of the present disclosure are directed to intravascular devices, systems, and methods.

In one embodiment, an intravascular system is provided. The system includes an intravascular device having a flexible elongate member having a proximal portion and a distal portion, at least one electronic component secured to the distal portion of the flexible elongate member, and at least one electrical connector secured to the proximal portion of the flexible elongate member, wherein the at least one electrical connector is electrically coupled to the at least one electronic component secured to the distal portion of the flexible elongate member. The system also includes a connector having at least one electrical contact configured to interface with the at least one electrical connector of the intravascular device. The connector includes a first connection piece and a second connection piece, wherein the first connection piece is movable relative to the second connection piece between an open position and a closed position. In the open position, an elongated opening is formed between the first and second connection pieces to facilitate insertion of the at least one electrical connector between the first and second connection pieces in a direction transverse to a longitudinal axis of the intravascular device. In the closed position, the at least one electrical contact is electrically coupled to the at least one electrical connector received between the first and second connection pieces.

In some embodiments, the first connection piece is movable relative to the second piece about a pivot axis. In some embodiments, the first connection piece is translatable relative to the second connection piece. Further, in some instances a bias element, such as a spring, urges the first and second connection pieces towards the closed position. In some arrangements, the second connection piece includes a recess sized and shaped to receive a portion of the intravascular device that includes the at least one electrical connector. In some embodiments, the first piece includes at least one visual indicator for aligning the at least one electrical contact of the connector with the at least one electrical connector of the intravascular device. The visual indicator is a light in some instances. In some particular instances, the light is configured to illuminate when a proper electrical coupling is achieved between the at least one electrical contact and the at least one electrical connector. In other instances, the light is configured to illuminate a first color when a proper electrical coupling is achieved between the at least one electrical contact and the at least one electrical connector and configured to illuminate a second color when the proper electrical coupling between the at least one electrical contact and the at least one electrical connector is not achieved.

In another embodiment, a method is provided. The method includes providing a connector having at least one electrical contact; moving the connector to an open position such an elongated opening is defined between a first component of the connector and a second component of the connector; inserting a connection portion of an intravascular device into the elongated opening and between the first and second components of the connector by moving the intravascular device in a direction transverse to a longitudinal axis of the intravascular device; and moving the connector to a closed position to electrically couple the at least one electrical contact of the connector to at least one electrical connector of the connection portion of the intravascular device positioned between the first and second components of the connector. In some instances, the at least one electrical connector is electrically connected to an electronic component positioned at a distal portion of the intravascular device such that the at least one electrical contact is electrically coupled to the electronic component when the at least one electrical contact is electrically coupled to the at least one electrical connector of the connection portion of the intravascular device. In some instances, the electronic component is a pressure sensing component. In some instances, the electronic component is an intravascular imaging component. For example, the intravascular imaging component may include one or more ultrasound transducer(s) and/or optical coherence tomography (OCT) imaging element(s). In some embodiments, the method also includes aligning at least one visual marker of the connector with the at least one electrical connector of the connection portion of the intravascular device.

In yet another embodiment, a connector for an intravascular system is provided. The connector includes a first connection piece and a second connection piece movably coupled to the first connection piece and having at least one electrical contact secured thereto. The second connection piece is movable relative to the first connection piece between an open position and a closed position, wherein in the open position an elongated opening is formed between the first and second connection pieces to facilitate insertion of a connection portion of an intravascular device between the first and second connection pieces in a direction transverse to a longitudinal axis of the intravascular device and wherein in the closed position the at least one electrical contact is electrically coupled to the connection portion of the intravascular device received between the first and second connection pieces.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which:

FIG. 1 is a diagrammatic perspective view of an intravascular system according to an embodiment of the present disclosure.

FIG. 2 is a diagrammatic side view of an intravascular device of the intravascular system of FIG. 1 according to an embodiment of the present disclosure.

FIG. 3 is a diagrammatic side view of an intravascular device of the intravascular system of FIG. 1 similar to that of FIG. 2, but illustrating another embodiment of the present disclosure.

FIG. 4 is a diagrammatic side view of a proximal connector portion of an intravascular device according to an embodiment of the present disclosure.

FIG. 42 is a diagrammatic rear view of the connector of FIGS. 32-41.

FIG. 43 is a diagrammatic rear view of the connector similar to that of FIG. 42, but with inner components of the connector illustrated.

DETAILED DESCRIPTION

Figure 5:
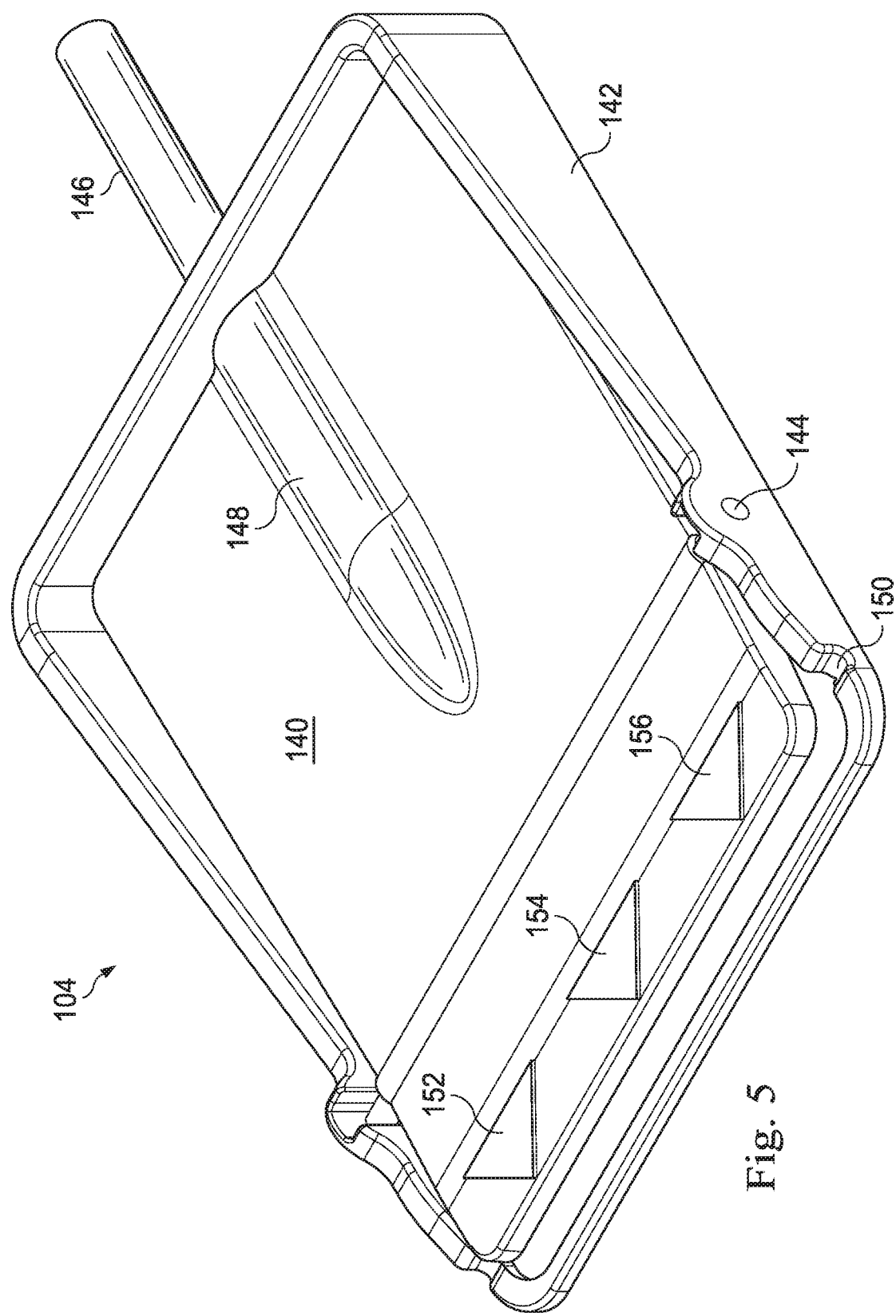
FIG. 5 is a diagrammatic perspective view of a connector of the intravascular system of FIG. 1 according to an embodiment of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

As used herein, "flexible elongate member" or "elongate flexible member" includes at least any thin, long, flexible structure that can be inserted into the vasculature of a patient. While the illustrated embodiments of the "flexible elongate members" of the present disclosure have a cylindrical profile with a circular cross-sectional profile that defines an outer diameter of the flexible elongate member, in other instances all or a portion of the flexible elongate members may have other geometric cross-sectional profiles (e.g., oval, rectangular, square, elliptical, etc.) or non-geometric cross-sectional profiles. Flexible elongate members include, for example, intravascular catheters and intravascular guidewires. In that regard, intravascular catheters may or may not include a lumen extending along its length for receiving and/or guiding other instruments. If the intravascular catheter includes a lumen, the lumen may be centered or offset with respect to the cross-sectional profile of the device.

In most embodiments, the flexible elongate members of the present disclosure include one or more electronic, optical, or electro-optical components. For example, without limitation, a flexible elongate member may include one or more of the following types of components: a pressure sensor, a temperature sensor, an imaging element, an optical fiber, an ultrasound transducer, a reflector, a mirror, a prism, an ablation element, an rf electrode, a conductor, and/or combinations thereof. Generally, these components are configured to obtain data related to a vessel or other portion of the anatomy in which the flexible elongate member is disposed. Often the components are also configured to communicate the data to an external device for processing and/or display. In some aspects, embodiments of the present disclosure include imaging devices for imaging within the lumen of a vessel, including both medical and non-medical applications. However, some embodiments of the present disclosure are particularly suited for use in the context of human vasculature. Imaging of the intravascular space, particularly the interior walls of human vasculature can be accomplished by a number of different techniques, including ultrasound (often referred to as intravascular ultrasound ("IVUS") and intracardiac echocardiography ("ICE")) and optical coherence tomography ("OCT"). In other instances, infrared, thermal, or other imaging modalities are utilized. Further, in some instances the flexible elongate member includes multiple electronic, optical, and/or electro-optical components (e.g., pressure sensors, temperature sensors, imaging elements, optical fibers, ultrasound transducers, reflectors, mirrors, prisms, ablation elements, rf electrodes, conductors, etc.).

The electronic, optical, and/or electro-optical components of the present disclosure are often disposed within a distal portion of the flexible elongate member. As used herein, "distal portion" of the flexible elongate member includes any portion of the flexible elongate member from the mid-point to the distal tip. As flexible elongate members can be solid, some embodiments of the present disclosure will include a housing portion at the distal portion for receiving the electronic components. Such housing portions can be tubular structures attached to the distal portion of the elongate member. Some flexible elongate members are tubular and have one or more lumens in which the electronic components can be positioned within the distal portion.

The electronic, optical, and/or electro-optical components and the associated communication lines are sized and shaped to allow for the diameter of the flexible elongate member to be very small. For example, the outside diameter of the elongate member, such as a guidewire or catheter, containing one or more electronic, optical, and/or electro-optical components as described herein are between about 0.0007" (0.0178 mm) and about 0.118" (3.0 mm), with some particular embodiments having outer diameters of approximately 0.014" (0.3556 mm) and approximately 0.018" (0.4572 mm)). As such, the flexible elongate members incorporating the electronic, optical, and/or electro-optical component(s) of the present application are suitable for use in a wide variety of lumens within a human patient besides those that are part or immediately surround the heart, including veins and arteries of the extremities, renal arteries, blood vessels in and around the brain, and other lumens.

"Connected" and variations thereof as used herein includes direct connections, such as being glued or otherwise fastened directly to, on, within, etc. another element, as well as indirect connections where one or more elements are disposed between the connected elements.

"Secured" and variations thereof as used herein includes methods by which an element is directly secured to another element, such as being glued or otherwise fastened directly to, on, within, etc. another element, as well as indirect techniques of securing two elements together where one or more elements are disposed between the secured elements.

Referring now to FIG. 1, shown therein is an intravascular system 100 according to an embodiment of the present disclosure. In that regard, the intravascular system includes an intravascular device 102 and a connector 104. Referring now to FIG. 2, a side view of the intravascular device 102 is provided. As shown, the intravascular device 102 includes a flexible elongate member 106 having a distal portion 107 adjacent a distal end 108 and a proximal portion 109 adjacent a proximal end 110. A component 112 is positioned within the distal portion 107 of the flexible elongate member 106 proximal of the distal tip 108. Generally, the component 112 is representative of one or more electronic, optical, or electro-optical components. In that regard, the component 112 is a pressure sensor, a temperature sensor, an imaging element, an optical fiber, an ultrasound transducer, a reflector, a mirror, a prism, an ablation element, an rf electrode, a conductor, and/or combinations thereof. The specific type of component or combination of components can be selected based on an intended use of the intravascular device. In some instances, the component 112 is positioned less than 10 cm, less than 5, or less than 3 cm from the distal tip 108. In some instances, the component 112 is positioned within a housing of the intravascular device 102. In that regard, the housing is a separate component secured to the flexible elongate member 106 in some instances. In other instances, the housing is integrally formed as a part of the flexible elongate member 106.

The intravascular device 102 also includes a connection portion 114 adjacent the proximal portion 109 of the device. In that regard, the connection portion 114 is spaced from the proximal end 110 of the flexible elongate member 106 by a distance 116. Generally, the distance 116 is between 0% and 50% of the total length of the flexible elongate member 106. While the total length of the flexible elongate member can be any length, in some embodiments the total length is between about 1300 mm and about 4000 mm, with some specific embodiments have a length of 1400 mm, 1900 mm, and 3000 mm. Accordingly, in some instances the connection portion 114 is positioned at the proximal end 110. In that regard, FIG. 3 illustrates an embodiment of an intravascular device 120 where the connection portion 114 is positioned at the proximal end 110. In other instances, the connection portion 114 is spaced from the proximal end 110. For example, in some instances the connection portion 114 is spaced from the proximal end 110 between about 0 mm and about 1400 mm. In some specific embodiments, the connection portion 114 is spaced from the proximal end by a distance of 0 mm, 300 mm, and 1400 mm.

The connection portion 114 is configured to facilitate communication between the intravascular device 102, 120 and another device. More specifically, in some embodiments the connection portion 114 is configured to facilitate communication of data obtained by the component 112 to another device, such as a computing device or processor. Accordingly, in some embodiments the connection portion 114 is an electrical connector. In such instances, the connection portion 114 is configured to provide an electrical connection to one or more electrical conductors that extend along the length of the flexible elongate member 102 and are electrically coupled to the component 112. In some instances, the connection portion 114 includes one or more electrical connectors as described in U.S. Patent Application No. 61/665,697, titled "INTRAVASCULAR DEVICES, SYSTEMS, AND METHODS," filed Jun. 28, 2012, which is hereby incorporated by reference in its entirety. In other embodiments, the connection portion 114 includes an optical connector. In such instances, the connection portion 114 provides an optical connection to one or more optical communication pathways (e.g., fiber optic cable) that extend along the length of the flexible elongate member 106 and are optically coupled to the component 112. Further, in some embodiments the connection portion 114 provides both electrical and optical connections to both electrical conductor(s) and optical communication pathway(s) coupled to the component 112. In that regard, it should again be noted that component 112 is comprised of a plurality of elements in some instances. In some instances, the connection portion 114 is configured to provide a physical connection to another device, either directly or indirectly. In other instances, the connection portion 114 is configured to facilitate wireless communication between the intravascular device 102 and another device. Generally, any current or future developed wireless protocol(s) may be utilized. In yet other instances, the connection portion 114 facilitates both physical and wireless connection to another device.

As noted above, in some instances the connection portion 114 provides a connection between the component 112 of the intravascular device 102, 120 and an external device. Accordingly, in some embodiments one or more electrical conductors, one or more optical pathways, and/or combinations thereof extend along the length of the flexible elongate member 106 between the connection portion 114 and the component 112 to facilitate communication between the connection portion 114 and the component 112. Generally, any number of electrical conductors, optical pathways, and/or combinations thereof can extend along the length of the flexible elongate member 106 between the connection portion 114 and the component 112. In some instances, between one and ten electrical conductors and/or optical pathways extend along the length of the flexible elongate member 106 between the connection portion 114 and the component 112. For the sake of clarity and simplicity, the embodiments of the present disclosure described below include three electrical conductors and, therefore, the connection portion 114 is described as having three separate electrical connections corresponding to the three electrical conductors.

For example, as shown in FIG. 4, in some instances the connection portion 114 includes conductive portions 122, 124, and 126 that are separated from one another and the main body of the flexible elongate member 106 by insulating portions 128, 130, 132, and 134. In that regard, the conductive portions 122, 124, and 126 are formed of a conductive material and are portions of a hypotube, a coil, and/or combinations thereof in some instances. It is understood that the total number of communication pathways and/or the number of electrical conductors and/or optical pathways is different in other embodiments and, therefore, the number of conductive portions (or optical connectors) included in connection portion is different as well. More specifically, the number of communication pathways and the number of electrical conductors and optical pathways extending along the length of the flexible elongate member 106 is determined by the desired functionality of the component 112 and the corresponding elements that define component 112 to provide such functionality. As a result, the number and type of connections provided by connection portion 114 are likewise determined by the desired functionality of the component 112, the corresponding elements that define component 112 to provide such functionality, and the communication needs for such elements.

Figure 6:
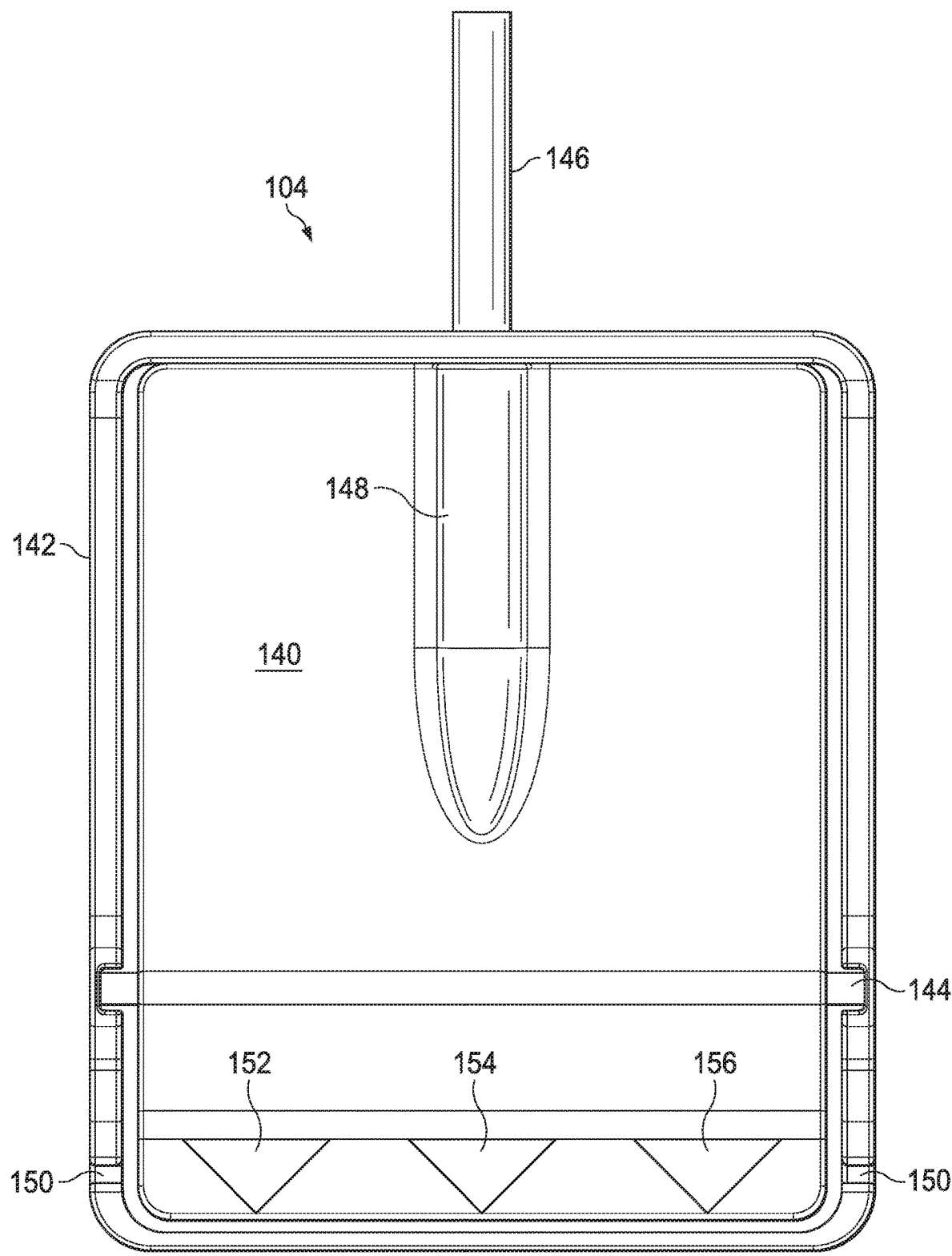
FIG. 6 is a diagrammatic top view of the connector of FIG. 5.
Figure 7:
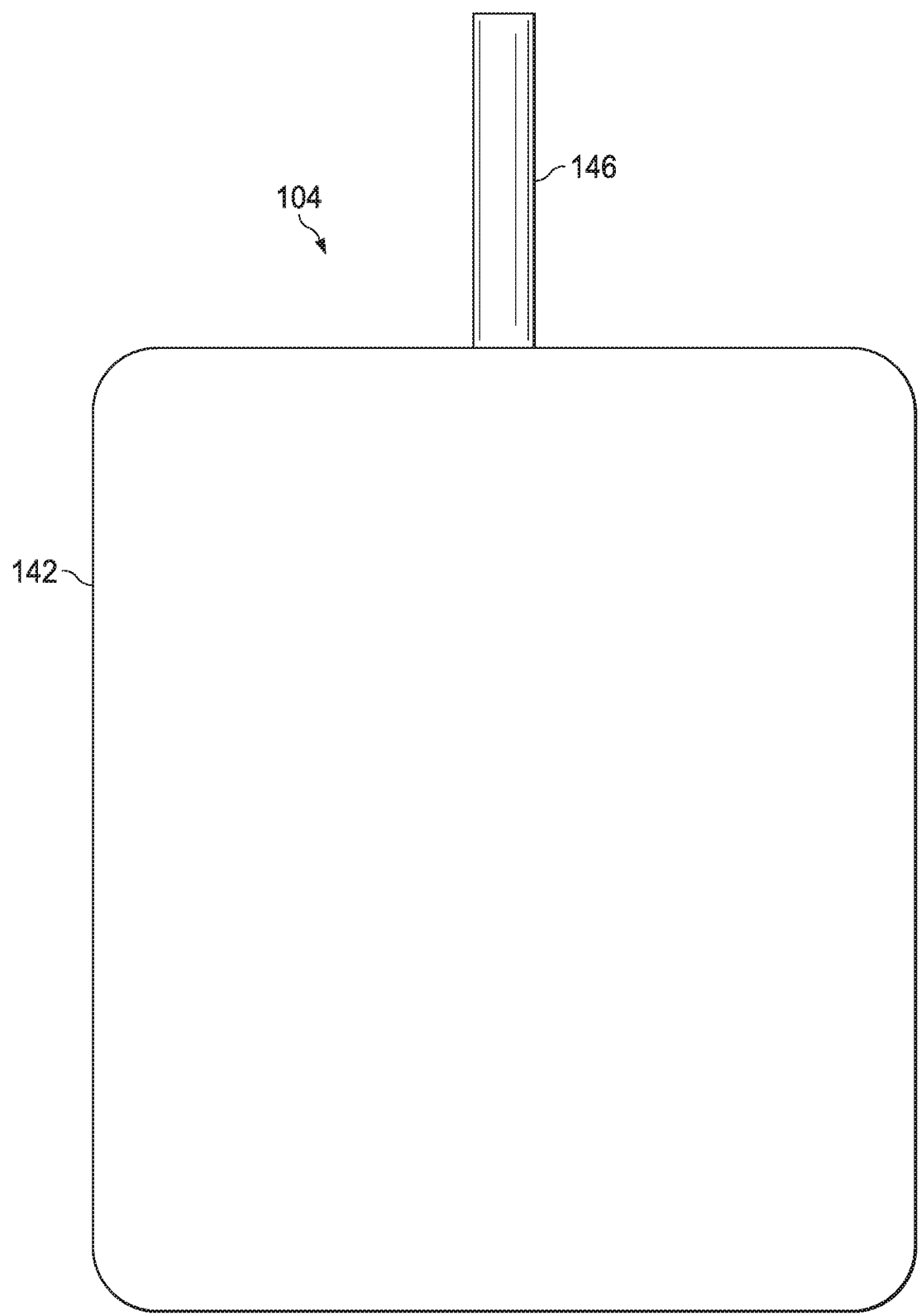
FIG. 7 is a diagrammatic bottom view of the connector of FIGS. 5 and 6.
Figure 8:
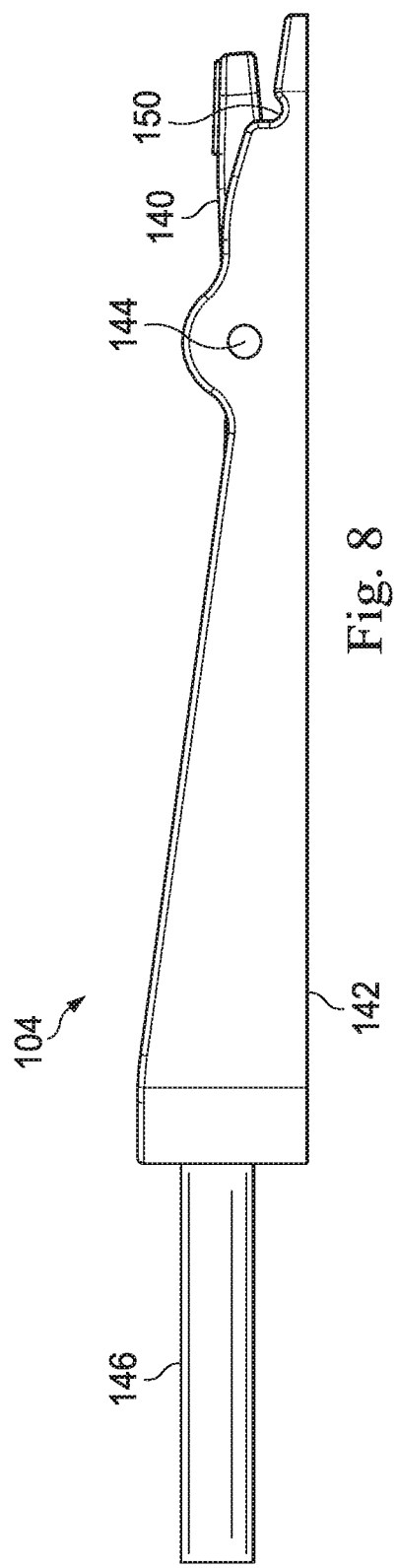
FIG. 8 is a diagrammatic side view of the connector of FIGS. 5-7.
Figure 9:
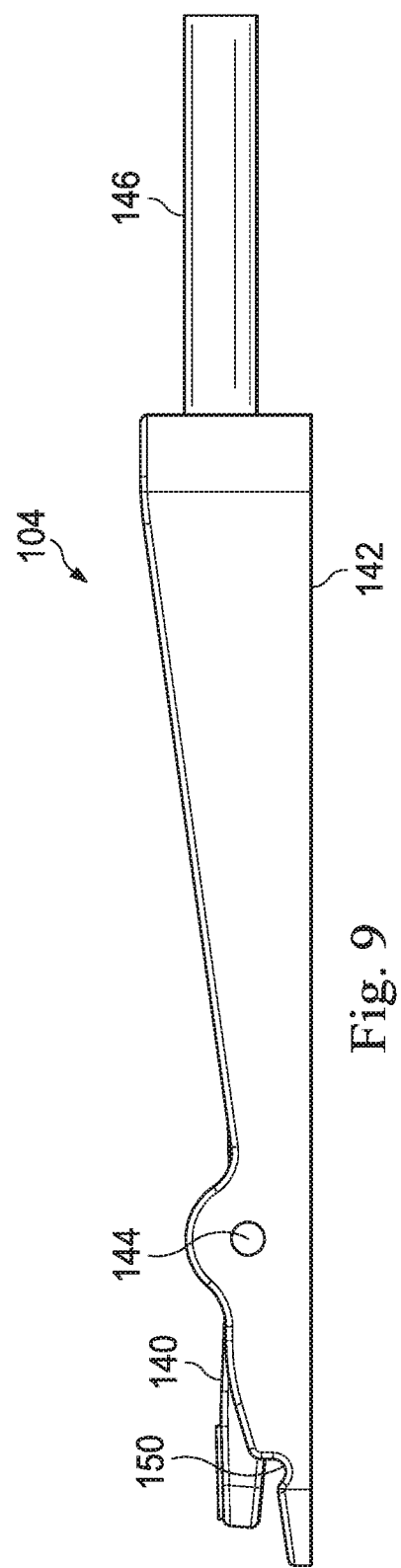
FIG. 9 is a diagrammatic side view of the connector of FIGS. 5-8 similar to that of FIG. 8, but from the opposite side of the connector.
Figure 10:
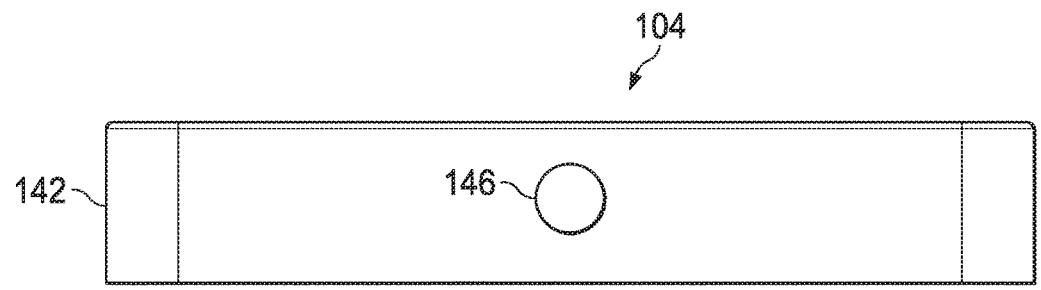
FIG. 10 is a diagrammatic rear view of the connector of FIGS. 5-9.
Figure 11:
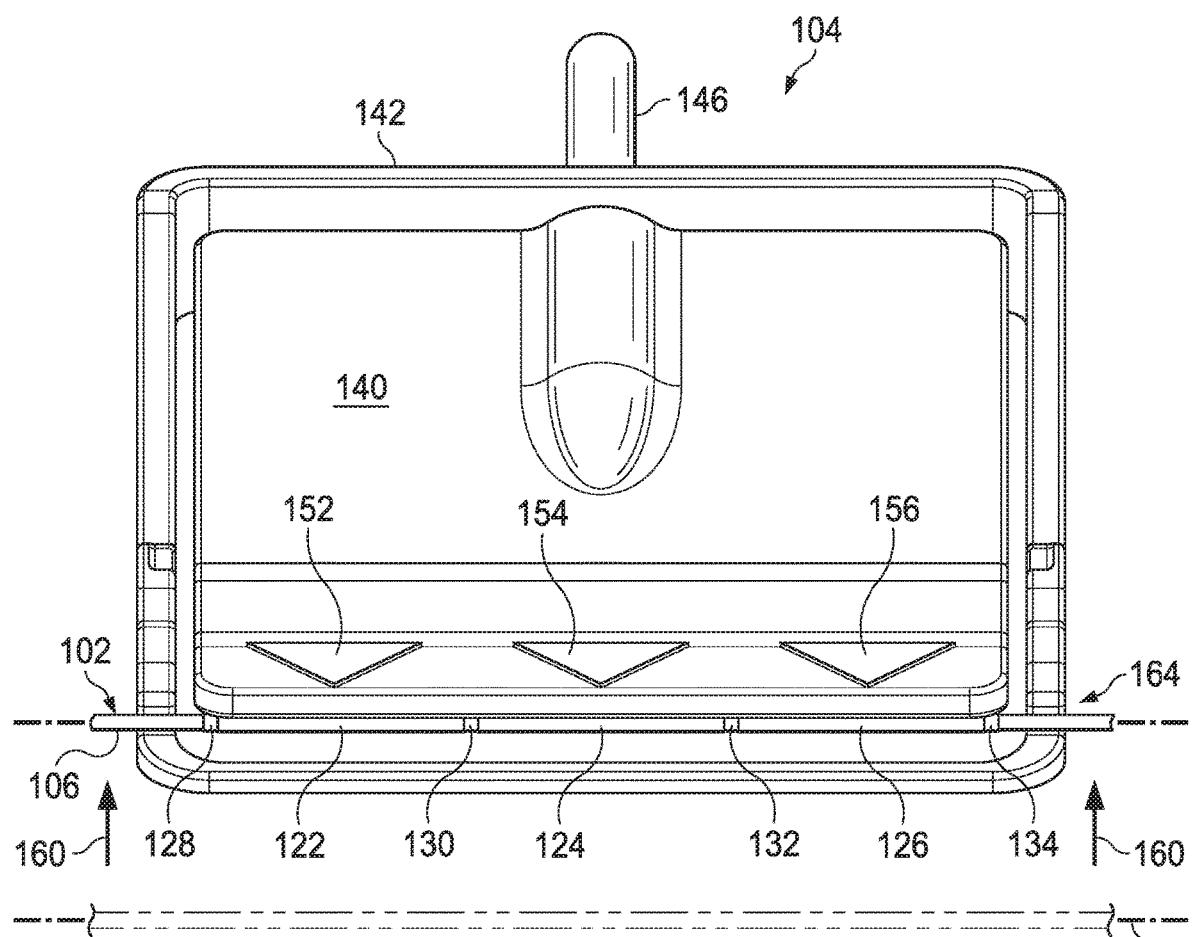
FIG. 11 is a diagrammatic perspective front view of the connector of FIGS. 5-10 shown in an open position and receiving an intravascular device according to an embodiment of the present disclosure.
Figure 12:
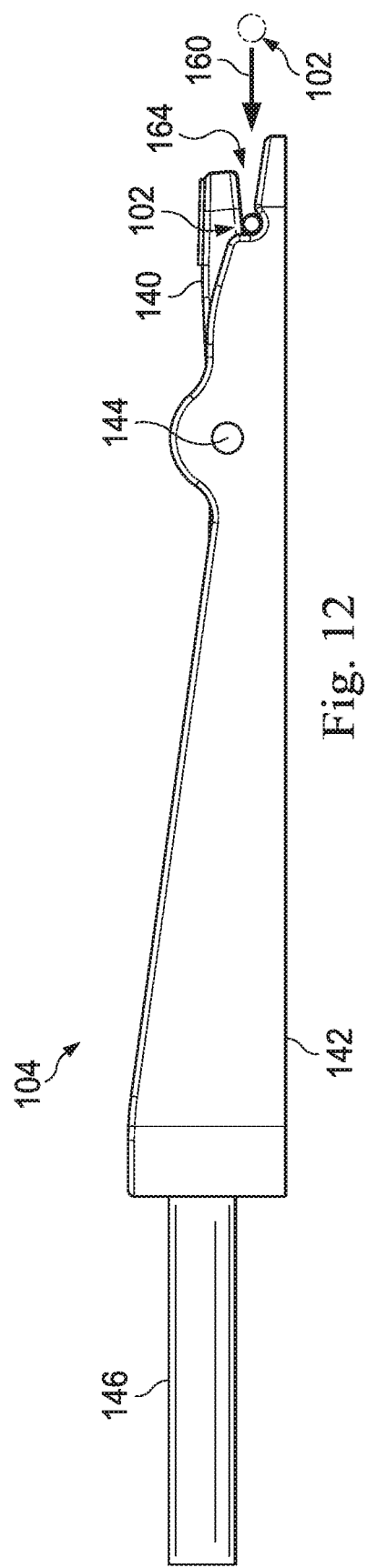
FIG. 12 is a diagrammatic side view of the connector of FIGS. 5-11 in the open position and receiving the intravascular device.

Referring now to FIGS. 5-12, shown therein are additional details of the connector 104. In that regard, FIG. 5 is a diagrammatic perspective view of the connector 104; FIG. 6 is a diagrammatic top view of the connector 104; FIG. 7 is a diagrammatic bottom view of the connector 104; FIG. 8 is a diagrammatic side view of the connector 104 from a first side; FIG. 9 is a diagrammatic side view of the connector 104 from a second side opposite the first side; FIG. 10 is a diagrammatic rear view of the connector 104; FIG. 11 is a diagrammatic perspective front view of the connector 104 shown in an open position and receiving the intravascular device 102; and FIG. 12 is a diagrammatic side view of the connector 104 and the intravascular device 102 in the arrangement of FIG. 11.

Connector 104 is configured to interface with the connection portion 114 of the intravascular device 102 to facilitate communication between the intravascular device 102 and a separate component, such as a processing system. In particular, the connector 104 is configured to facilitate communication between one or more electronic components of the intravascular device 102 that are electrically coupled to the connection portion 114 and a separate component, such as a processing system associated with the one or more electronic components. As shown in FIG. 5, the connector 104 includes an upper connection piece 140 and a lower connection piece 142. In the illustrated embodiment, the upper connection piece 140 is movable with respect to the lower connection piece 142 about a pivot pin 144. In some instances, the pivot pin 144 is fixedly secured to the lower connection piece 142. Further, the pivot pin 144 extends through a portion of the upper connection piece 140 and/or engages a structural feature of the upper connection piece (e.g., recess(es), clamp(s), snap-fit element(s), projection(s), etc.) to ensure that the upper connection piece 140 pivots about the pivot pin 144. In some embodiments, the upper connection piece 140 is biased towards either an open position (for receiving the connection portion 114 of the intravascular device 102) or closed position (for electrically coupling to the connection portion 114 of the intravascular device 102) by a bias element. For example, in some instances the bias element is configured to bias the connection piece 140 towards a closed position such that a user can release the connector 104 after insertion of the intravascular device and the bias element will maintain the connector 104 in electrical contact with the connection portion 114 of the intravascular device. In some instances, the bias element is a spring. In some particular instances, at least a portion of the spring is wrapped around the pivot pin 144. In that regard, the pivoting motion of the upper connection piece 140 relative to the lower connection piece 142, and the structural arrangements to facilitate such motion, operates in a manner to a clothes pin or a chip clip.

As noted above, the connector 104 is configured to interface with the connection portion 114 of the intravascular device 102 to facilitate communication between the intravascular device 102 and a separate component, and, in particular, the connector 104 is configured to facilitate communication between one or more electronic components of the intravascular device 102 (that are electrically coupled to the connection portion 114) and a separate component, such as a processing system associated with the one or more electronic components. To that end, the connector 104 includes a communication cable 146 extending therefrom. The communication cable 146 is configured to carry signals between the connector 104 and the separate component. In the illustrated embodiment, the cable 146 is configured to carry electrical signals and includes one or more electrical conductors extending along its length to facilitate such electrical communication. However, the type of communication cable utilized is dependent on the type of electronic, optical, and/or electro-optical components that are incorporated into the intravascular device 102. In that regard, the communication cable 146 may include one or more of an electrical conductor, an optical fiber, and/or combinations thereof. In some instances, the cable 146 is configured to be plugged into an interface of a processing system. In that regard, the interface is a patient interface module (PIM) in some instances.

As shown in FIG. 6, for example, the cable 146 extends through an opening on the back side of the lower connection piece 142. The upper connection piece 140 includes a projection or protrusion 148 in its upper surface that defines a corresponding recess or opening thereunder for receiving at least a portion of the cable 146. In that regard, in some instances one or more electrical conductors of the cable 146 are positioned within the recess or opening defined by the protrusion 148. Further, the one or more electrical conductors of the cable 146 are electrically coupled to one or more electrical contacts associated with the connector 104. In that regard, in some embodiments the electrical contacts are fixedly secured to the upper connection piece 140. In some such instances, the one or more electrical conductors of the cable 146 are soldered to the electrical contacts of the upper connection piece. However, in other embodiments, the electrical contacts are fixedly secured to the lower connection piece 142. In some instances, gold plated copper alloy contacts are utilized. However, it is understood that any suitable electrical contacts can be utilized by the connector 104.

In some instances, the cable 146 is replaced with a wireless connection (e.g., a wireless antenna). In that regard, it is understood that various communication pathways between the connector 104 and another component of the intravascular system may be utilized, including physical connections (including electrical, optical, and/or fluid connections), wireless connections, and/or combinations thereof.

As shown in FIGS. 5, 8, 9, 11, and 12, the lower connection piece 142 includes a recess 150 that is sized and shaped to receive the intravascular device 102 therein. In particular, the recess 150 is sized and shaped to receive the connection portion 114 of the intravascular device 102. In that regard, the width of the recess 150 is typically sized to be slightly larger than the diameter of the connection portion 114 of the intravascular device 102. The recess 150 helps to maintain the connection portion 114 of the intravascular device 102 in position within the connector 104. To help ensure that the connection portion 114 of the intravascular device 102 is properly aligned with the electrical contacts of the connector 104, the upper connection piece 140 includes visual markers 152, 154, and 156 that provide an indication of the location of the electrical contacts and, therefore, where the electrical contacts or connectors of the connection portion 114 of the intravascular device 102 should be aligned. For example, as shown in FIG. 11, the visual markers 152, 154, and 156 are configured to be aligned with the conductive portions 122, 124, and 126, respectively, of connection portion 114 to facilitate connection of the connector 104 to the intravascular device 102.

In the illustrated embodiment, the visual markers 152, 154, and 156 are arrows. However, it is understood that any type of visual markers may be utilized including, without limitation, projections, recesses, colors, shapes, and/or combinations thereof. In that regard, in some embodiments the visual markers are color-coded to match correspondingly colored visual markers associated with the electrical contacts or connectors of the intravascular device 102. Further, as discussed below with respect to FIGS. 13 and 14, in some embodiments of the present disclosure the connector 104 includes an active element to provide an indication of whether a proper connection between the connector and the connection portion 114 of the intravascular device 102 has been achieved. The active element may provide a visual signal, an audible signal, and/or combinations thereof representing a connection between the connector 104 and the connection portion 114. For example, in some instances a first indicator (e.g., a first color, symbol, sound, combinations thereof, etc.) is associated with no connection or an improper connection, while a second indicator (e.g., a second color, symbol, sound, combinations thereof, etc.) is associated with a proper electrical connection. It is understood that the two indicators simply need to be distinguishable from one another. Accordingly, in some instances, one of the indicators provides no indication at all (i.e., a null or zero value indicator). Generally, any combination of distinguishable indicators may be used. Further, in some instances, the active element may have intermediate indicator positions indicating partial connection(s) between the connector 104 and the connection portion 114. In one particular example, the active element has a first indicator (e.g., a first color (e.g., red), symbol, sound, combinations thereof, etc.) when no connection is made, a second indicator (e.g., a second color (e.g., yellow), symbol, sound, combinations thereof, etc.) when a partial connection is made, and a third indicator (e.g., a third color (e.g., green), symbol, sound, combinations thereof, etc.) when a full connection is made. Above, the active element has been described as being applicable to the overall connection between the connector 104 and the connection portion 114. However, in other embodiments, an active element is provided for each connection between a conductor of the connector 104 and a conductor of the connection portion 114. Further still, in some embodiments at least some portions of the connector 104 are formed of a clear or translucent material that allows visual verification that the contacts of the connector 104 are aligned with the contacts of intravascular device 102.

The connector 104 is configured to receive the intravascular device 102 in a side-loading fashion. More specifically, the connector 104 is configured to receive the connection portion 114 of the intravascular device 102 in a direction that is transverse to the longitudinal axis of the intravascular device. For example, referring more specifically to FIGS. 11 and 12, connector 104 is configured to receive the connection portion 114 in the direction of arrow 160 that extends transverse or perpendicular to the longitudinal axis 162 of the intravascular device 102. In that regard, upper connection piece 140 and lower connection piece 142 are shown in an open position such that an elongated opening 164 is formed between the upper and lower connection pieces 140, 142 to facilitate insertion of the connection portion 114 between the upper and lower connection pieces in a direction 160 transverse to the longitudinal axis 162 of the intravascular device 102. In that regard, the opening 164 provides access to the recess 150 in the lower connection piece 142 that is configured to receive the intravascular device 102 such that the intravascular device 102 can be inserted into opening 164 in the direction 160 transverse to the longitudinal axis 162 of the intravascular device 102 and seated within the recess 150. With the intravascular device 102 positioned between the upper and lower connection pieces 140, 142, the upper and lower connection pieces are moved from the open position to a closed position. In the closed position, the intravascular device 102 is held between the upper and lower connection pieces 140, 142 such that the connector 104 is in electrical communication with the connection portion 114. In that regard, the upper connection pieces 140, 142 are biased towards the closed position by a bias element in some instances. Further, in some instances the connector 104 includes a locking element for securing the upper and lower connection pieces 140, 142 in the closed position. Generally, any type of mechanical locking mechanism may be used. In that regard, in some instances a locking mechanism is utilized to secure the connector 104 to the open position.

To load the intravascular device 102 within the connector 104 the connector 104 may be moved relative to the intravascular device 102, the intravascular device 102 may be moved relative to the connector 104, and/or combinations thereof. The side-loading functionality of the connector 104 provides easy electrical coupling and releasing of the connector 104 to the intravascular device 102. Also, the side-loading approach is less likely to lead to kinking or unwanted bending of the connection portion 114 that causes unwanted structural damage to the intravascular device 102. Further, when the connection portion 114 is spaced from the proximal end of the intravascular device 102, there is no need to feed the proximal end of the intravascular device through the connector 104 to electrically couple the connector to the intravascular device. As a result of these advantages, surgical procedures are improved from both a workflow standpoint as well as a quality of service standpoint, as users are more inclined to decouple the connector 104 from the intravascular device 102 when advancing the intravascular device within a patient, which provides better control of the intravascular device.

Figure 13:
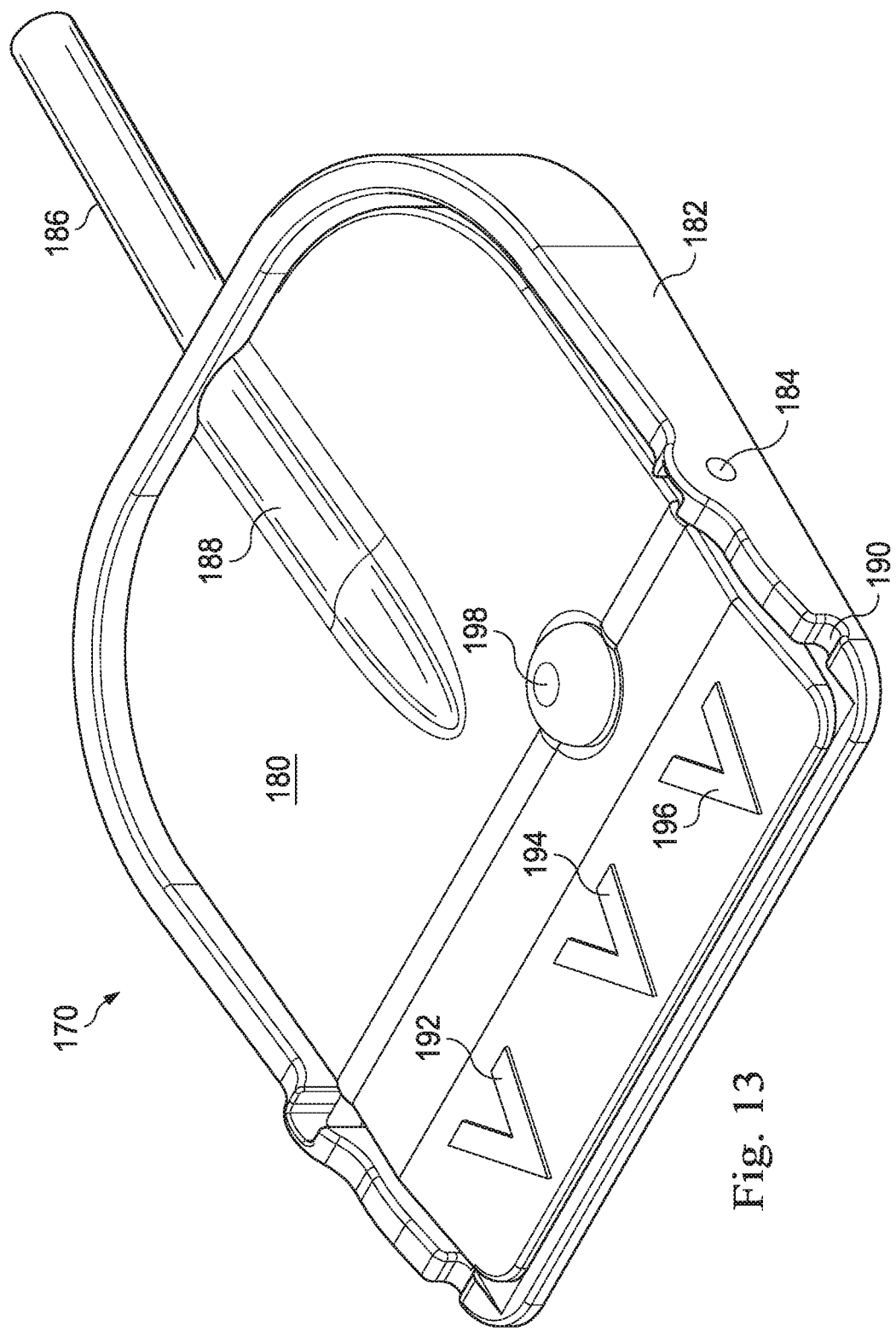
FIG. 13 is a diagrammatic perspective view of a connector of the intravascular system of FIG. 1 according to another embodiment of the present disclosure.
Figure 14:
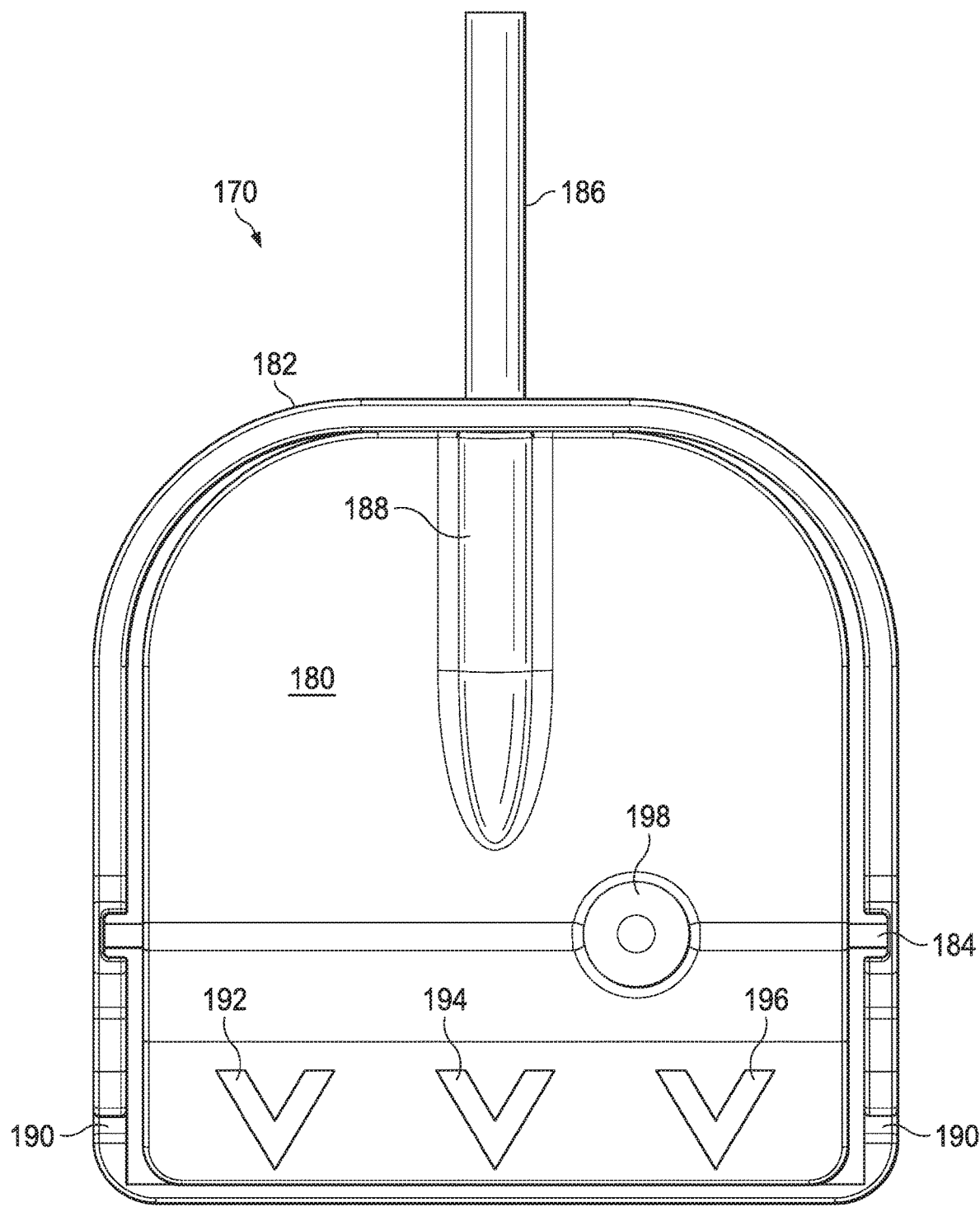
FIG. 14 is a diagrammatic top view of the connector of FIG. 13.

Referring now to FIGS. 13 and 14, shown therein is a connector 170 according to another embodiment of the present disclosure. In that regard, connector 170 includes some features similar to connector 104 described above. However, connector 170 includes an active element for indicating a connection state of the connector 170. Connector 170 is configured to interface with the connection portion 114 of the intravascular device 102 to facilitate communication between the intravascular device 102 and a separate component, such as a processing system. In particular, the connector 170 is configured to facilitate communication between one or more electronic components of the intravascular device 102 that are electrically coupled to the connection portion 114 and a separate component, such as a processing system associated with the one or more electronic components. As shown in FIG. 13, the connector 170 includes an upper connection piece 180 and a lower connection piece 182. In the illustrated embodiment, the upper connection piece 180 is movable with respect to the lower connection piece 182 about a pivot pin 184. In some instances, the pivot pin 184 is fixedly secured to the lower connection piece 182. Further, the pivot pin 184 extends through a portion of the upper connection piece 180 and/or engages a structural feature of the upper connection piece (e.g., recess(es), clamp(s), snap-fit element(s), projection(s), etc.) to ensure that the upper connection piece 180 pivots about the pivot pin 184.

In some embodiments, the upper connection piece 180 is biased towards either an open position (for receiving the connection portion 114 of the intravascular device 102) or closed position (for electrically coupling to the connection portion 114 of the intravascular device 102) by a bias element. For example, in some instances the bias element is configured to bias the connection piece 180 towards a closed position such that a user can release the connector 170 after insertion of the intravascular device and the bias element will maintain the connector 170 in electrical contact with the connection portion 114 of the intravascular device. In some instances, the bias element is a spring. In some particular instances, at least a portion of the spring is wrapped around the pivot pin 184. In that regard, the pivoting motion of the upper connection piece 180 relative to the lower connection piece 182, and the structural arrangements to facilitate such motion, operates in a manner to a clothes pin or a chip clip.

As noted above, the connector 170 is configured to interface with the connection portion 114 of the intravascular device 102 to facilitate communication between the intravascular device 102 and a separate component, and, in particular, the connector 104 is configured to facilitate communication between one or more electronic components of the intravascular device 102 (that are electrically coupled to the connection portion 114) and a separate component, such as a processing system associated with the one or more electronic components. To that end, the connector 170 includes a communication cable 186 extending therefrom. The communication cable 186 is configured to carry signals between the connector 170 and the separate component. In the illustrated embodiment, the cable 186 is configured to carry electrical signals and includes one or more electrical conductors extending along its length to facilitate such electrical communication. However, the type of communication cable utilized is dependent on the type of electronic, optical, and/or electro-optical components that are incorporated into the intravascular device 102. In that regard, the communication cable 186 may include one or more of an electrical conductor, an optical fiber, and/or combinations thereof. In some instances, the cable 186 is configured to be plugged into an interface of a processing system. In that regard, the interface is a patient interface module (PIM) in some instances.

As shown in FIG. 14, for example, the cable 186 extends through an opening on the back side of the lower connection piece 182. The upper connection piece 180 includes a projection or protrusion 188 in its upper surface that defines a corresponding recess or opening thereunder for receiving at least a portion of the cable 186. In that regard, in some instances one or more electrical conductors of the cable 186 are positioned within the recess or opening defined by the protrusion 188. Further, the one or more electrical conductors of the cable 186 are electrically coupled to one or more electrical contacts associated with the connector 170. In that regard, in some embodiments the electrical contacts are fixedly secured to the upper connection piece 180. In some such instances, the one or more electrical conductors of the cable 186 are soldered to the electrical contacts of the upper connection piece. However, in other embodiments, the electrical contacts are fixedly secured to the lower connection piece 182. In some instances, gold plated copper alloy contacts are utilized. However, it is understood that any suitable electrical contacts can be utilized by the connector 170.

In some instances, the cable 186 is replaced with a wireless connection (e.g., a wireless antenna). In that regard, it is understood that various communication pathways between the connector 170 and another component of the intravascular system may be utilized, including physical connections (including electrical, optical, and/or fluid connections), wireless connections, and/or combinations thereof.

As shown in FIGS. 13 and 14, the lower connection piece 182 includes a recess 190 that is sized and shaped to receive the intravascular device 102 therein. In particular, the recess 190 is sized and shaped to receive the connection portion 114 of the intravascular device 102. In that regard, the width of the recess 190 is typically sized to be slightly larger than the diameter of the connection portion 114 of the intravascular device 102. The recess 190 helps to maintain the connection portion 114 of the intravascular device 102 in position within the connector 170. To help ensure that the connection portion 114 of the intravascular device 102 is properly aligned with the electrical contacts of the connector 170, the upper connection piece 180 includes visual markers 192, 194, and 196 that provide an indication of the location of the electrical contacts and, therefore, where the electrical contacts or connectors of the connection portion 114 of the intravascular device 102 should be aligned. For example, similar to the visual markers 152, 154, and 156 of connector 104 shown in FIG. 11, the visual markers 192, 194, and 196 are configured to be aligned with the conductive portions 122, 124, and 126, respectively, of connection portion 114 to facilitate connection of the connector 170 to the intravascular device 102.

In the illustrated embodiment, the visual markers 192, 194, and 196 are arrows. However, it is understood that any type of visual markers may be utilized including, without limitation, projections, recesses, colors, shapes, and/or combinations thereof. In that regard, in some embodiments the visual markers are color-coded to match correspondingly colored visual markers associated with the electrical contacts or connectors of the intravascular device 102. Further, in the illustrated embodiment the connector 170 includes an active element 198 to provide an indication of whether a proper connection between the connector 170 and the connection portion 114 of the intravascular device 102 has been achieved. The active element may provide a visual signal, an audible signal, and/or combinations thereof representing a connection between the connector 170 and the connection portion 114. In the illustrated embodiment, active element 198 is a light emitting diode (LED) that illuminates when a proper connection is achieved between the connector 170 and the connection portion 114. For example, in some instances the active element 198 is off when no connection or an improper connection and illuminates when a proper connection is made. In other instances, the active element 198 illuminates a first color (e.g., red) when no connection or an improper connection is made and illuminates a second, different color (e.g., green) when a proper connection is made. In yet other instances, the active element 198 illuminates a first color (e.g., red) when no connection or an improper connection is made, illuminates a second, different color (e.g., yellow) when a partial connection is made, and illuminates a third, different color (e.g., green) when a full proper connection is made. The active element 198 has been described as being applicable to the overall connection between the connector 170 and the connection portion 114. However, in other embodiments, a separate active element is provided for each connection between a conductor of the connector 170 and a conductor of the connection portion 114.

Figure 15:
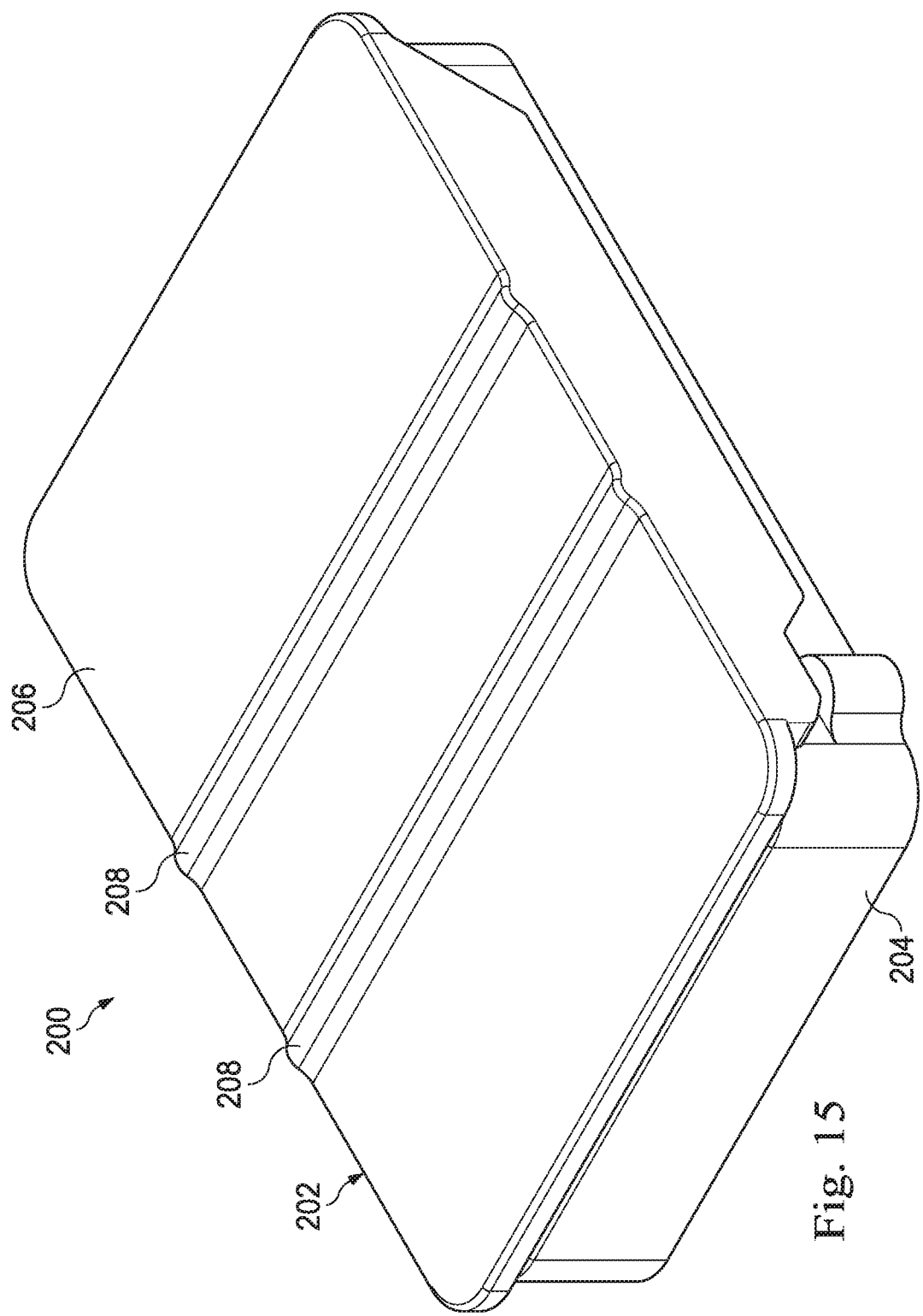
FIG. 15 is a diagrammatic perspective front view of a connector of the intravascular system of FIG. 1 according to yet another embodiment of the present disclosure.
Figure 16:
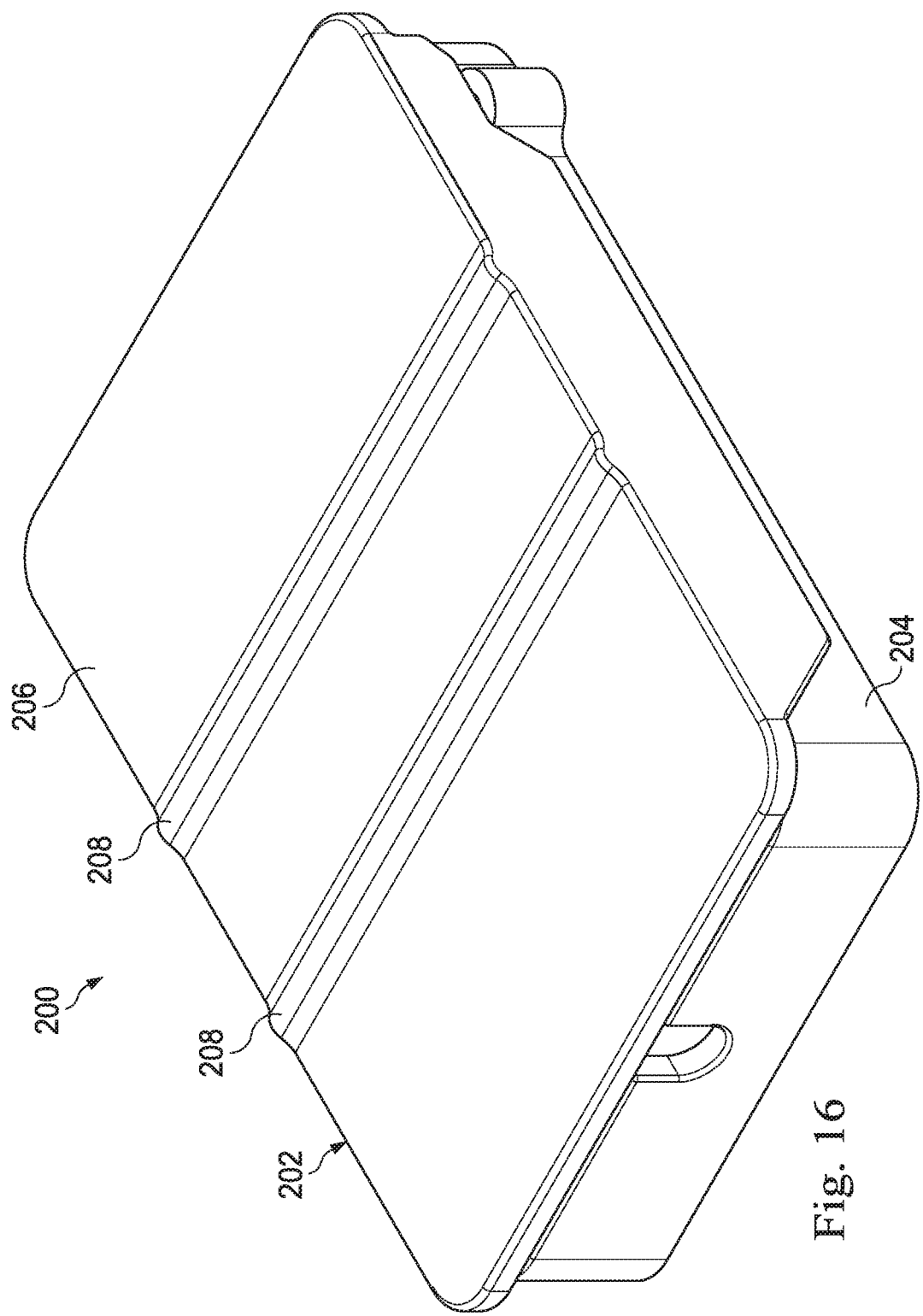
FIG. 16 is a diagrammatic perspective rear view of the connector of FIG. 15.
Figure 17:
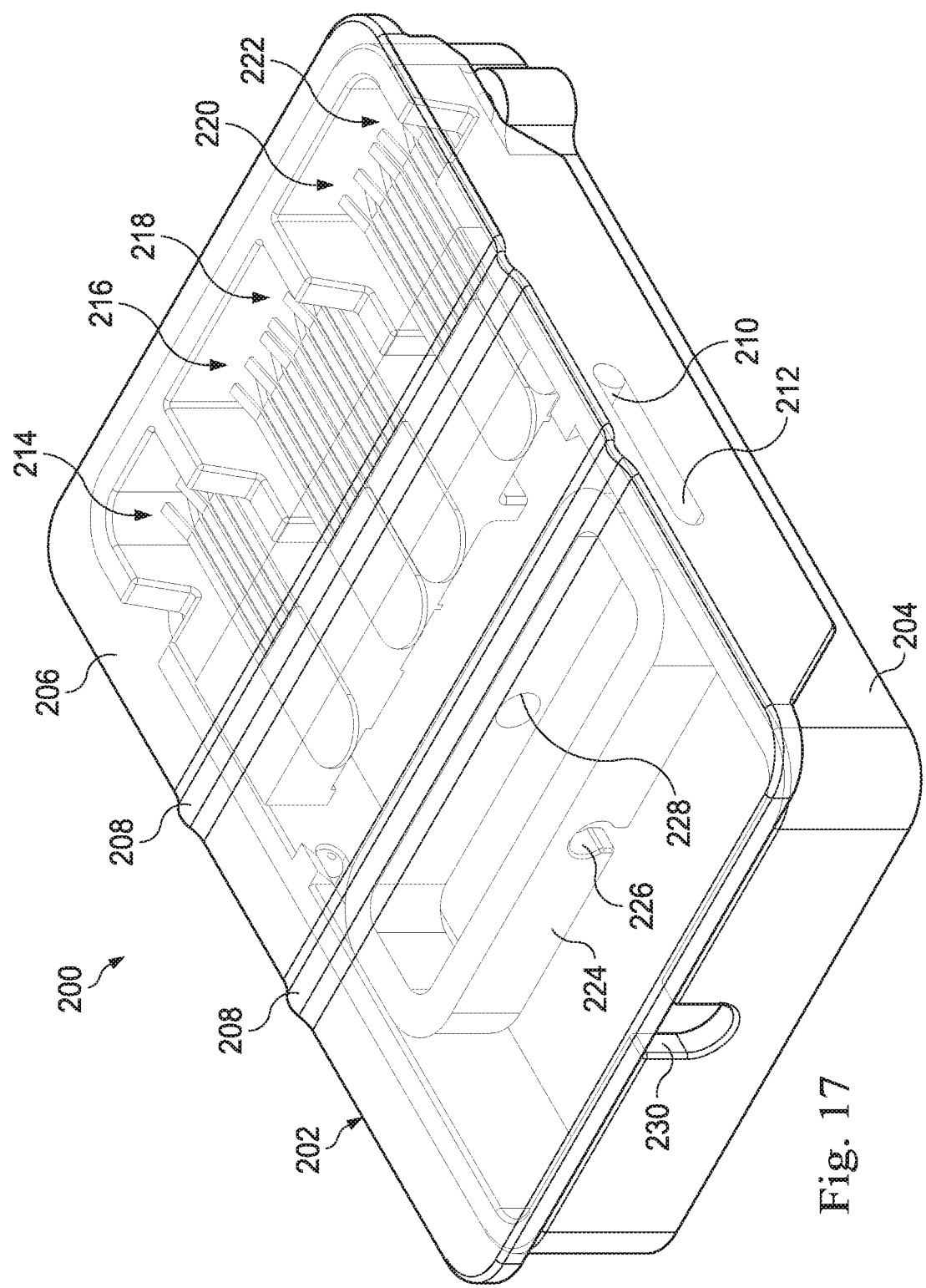
FIG. 17 is a diagrammatic perspective rear view of the connector similar to that of FIG. 16, but with inner components of the connector illustrated.
Figure 18:
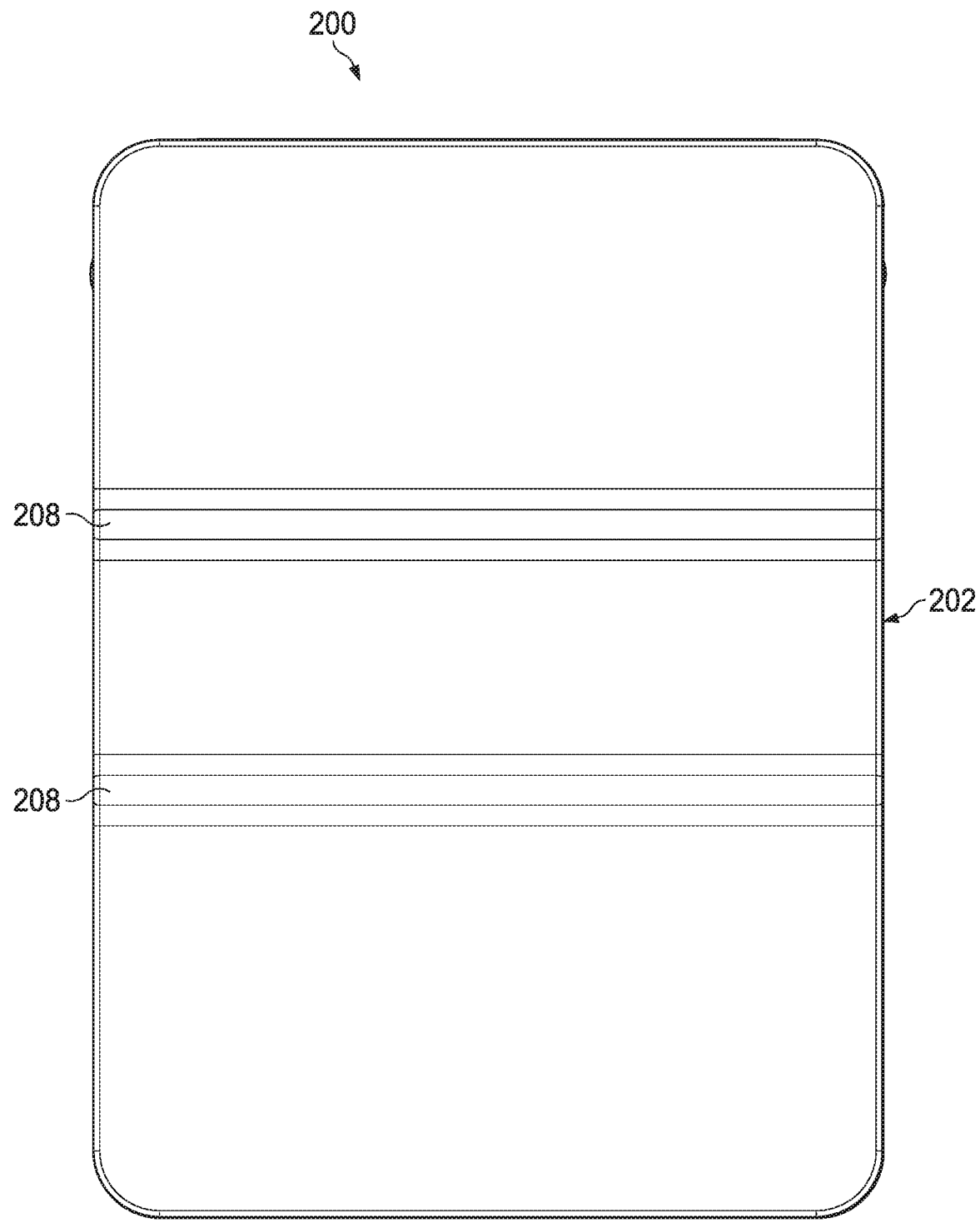
FIG. 18 is a diagrammatic top view of the connector of FIGS. 15-17.
Figure 19:
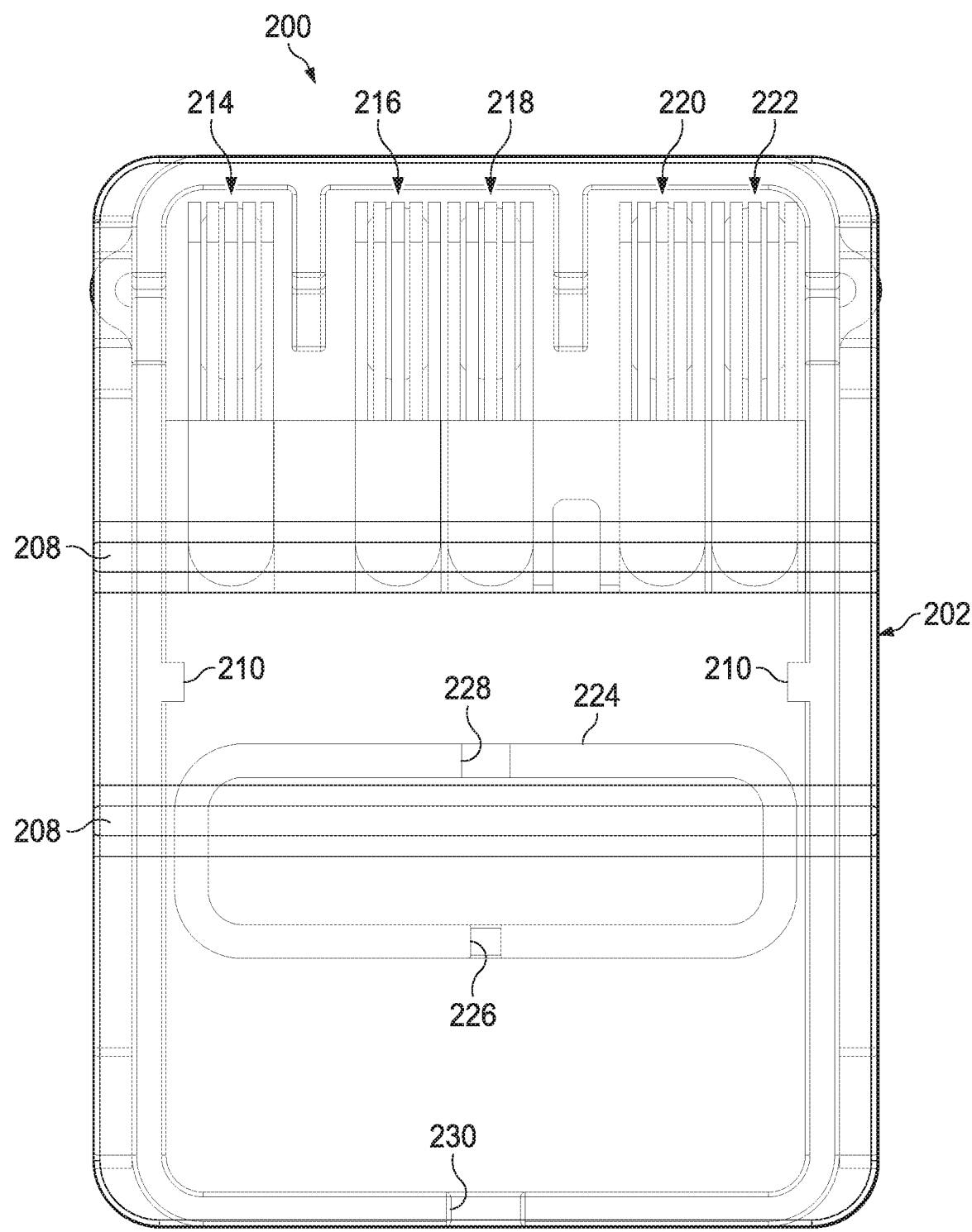
FIG. 19 is a diagrammatic top view of the connector similar to that of FIG. 18, but with the inner components of the connector illustrated.
Figure 20:
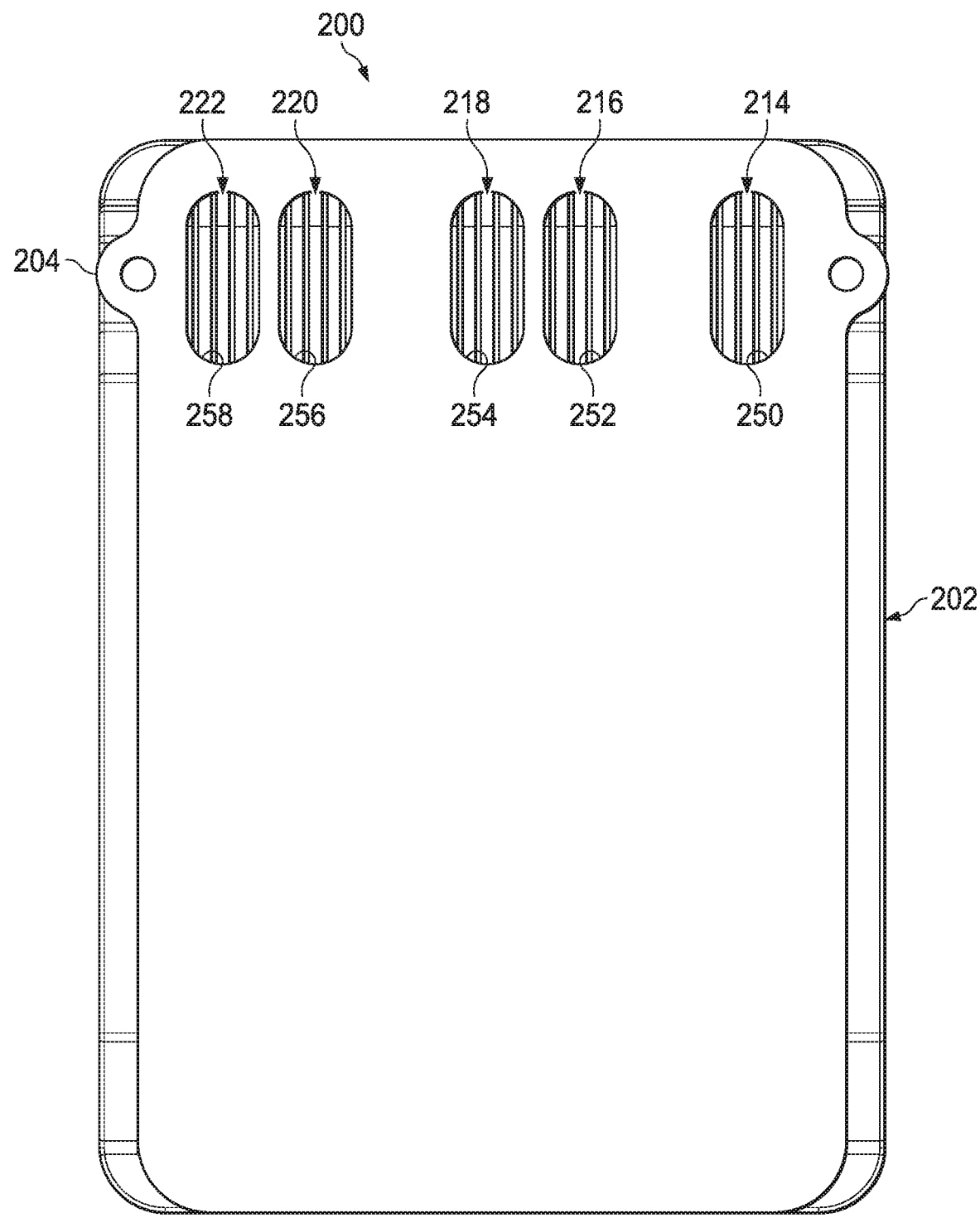
FIG. 20 is a diagrammatic bottom view of the connector of FIGS. 15-19.
Figure 21:
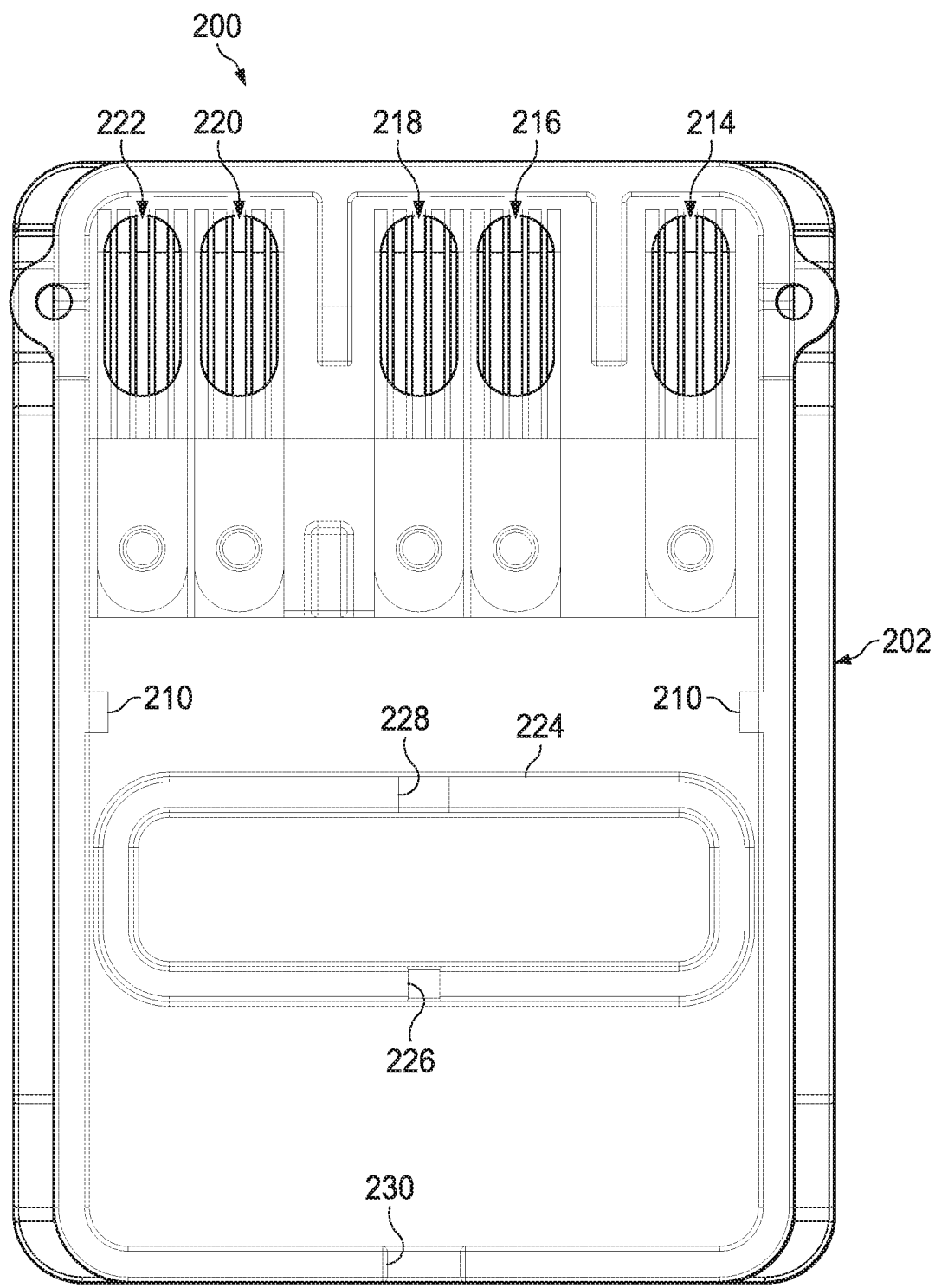
FIG. 21 is a diagrammatic bottom view of the connector similar to that of FIG. 20, but with the inner components of the connector illustrated.
Figure 22:
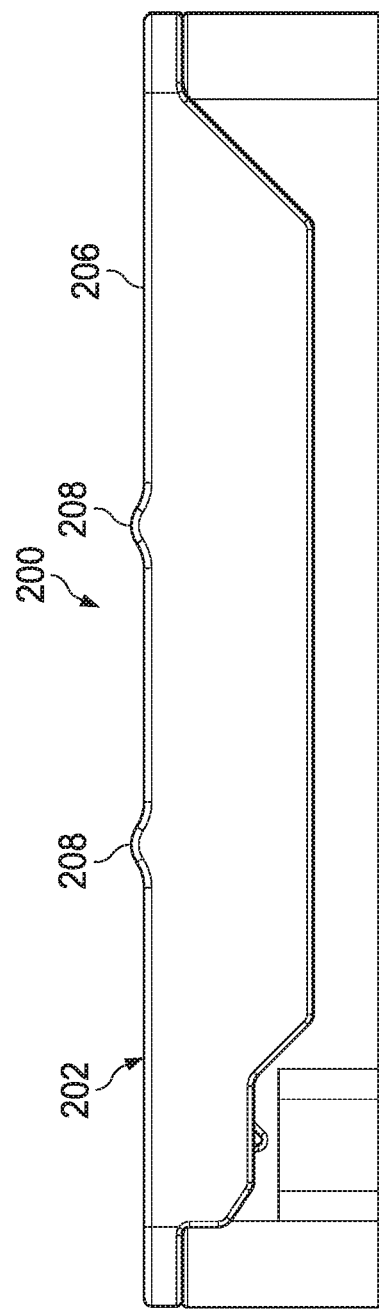
FIG. 22 is a diagrammatic side view of the connector of FIGS. 15-21.
Figure 23:
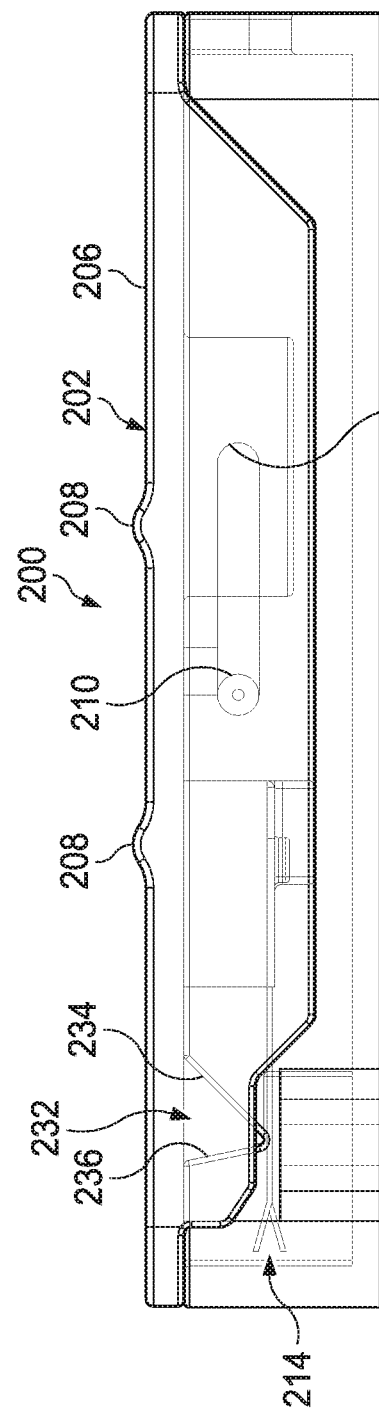
FIG. 23 is a diagrammatic side view of the connector similar to that of FIG. 22, but with inner components of the connector illustrated.
Figure 24:
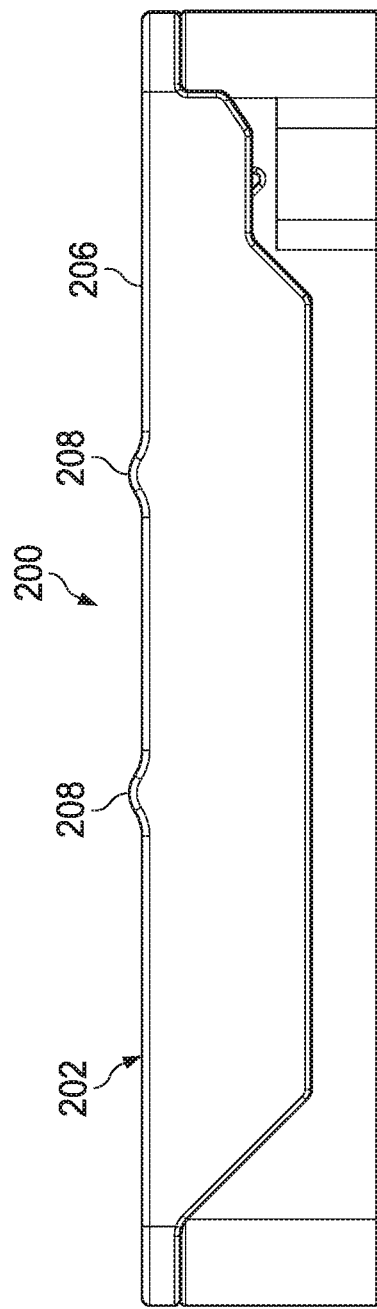
FIG. 24 is a diagrammatic side view of the connector of FIGS. 15-23 similar to that of FIG. 22, but from the opposite side of the connector.
Figure 25:
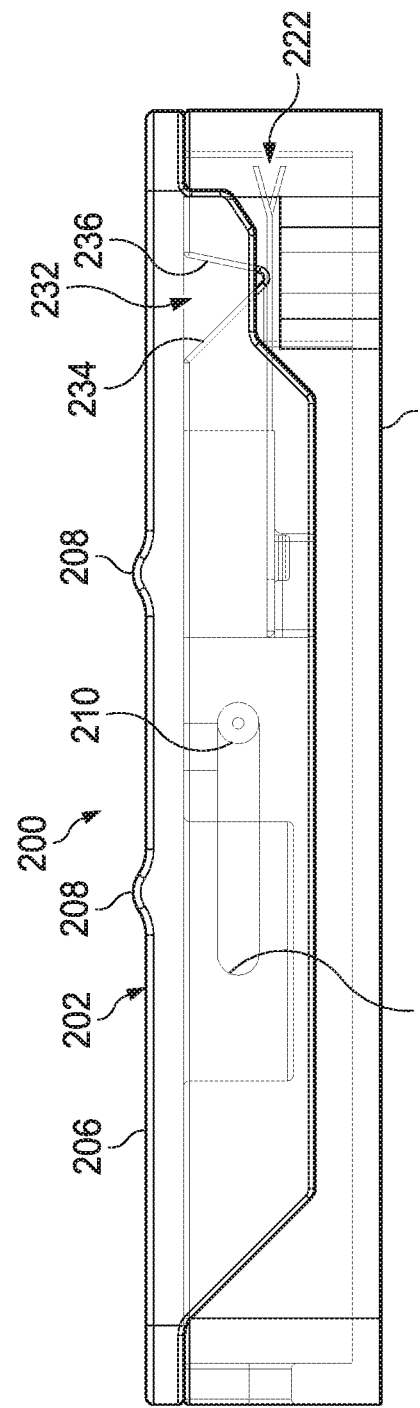
FIG. 25 is a diagrammatic side view of the connector similar to that of FIG. 24, but with inner components of the connector illustrated.
Figure 26:
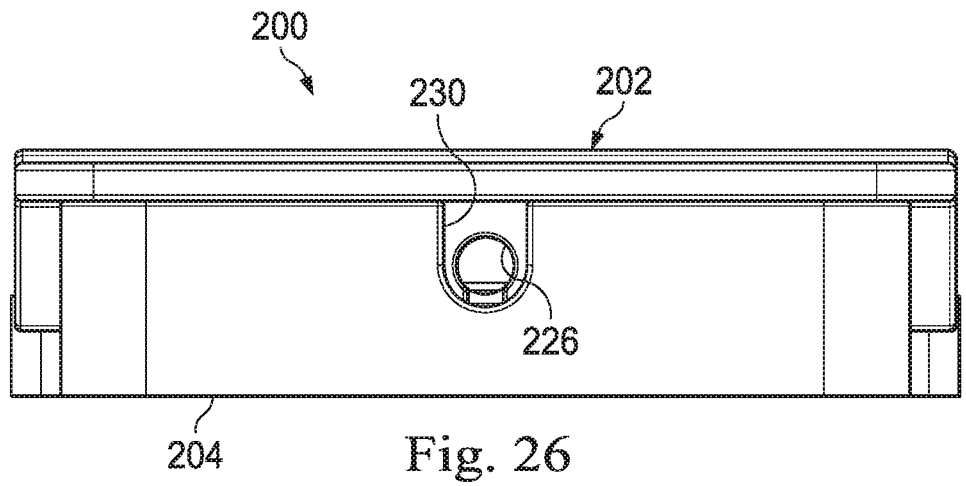
FIG. 26 is a diagrammatic rear view of the connector of FIGS. 15-25.
Figure 27:
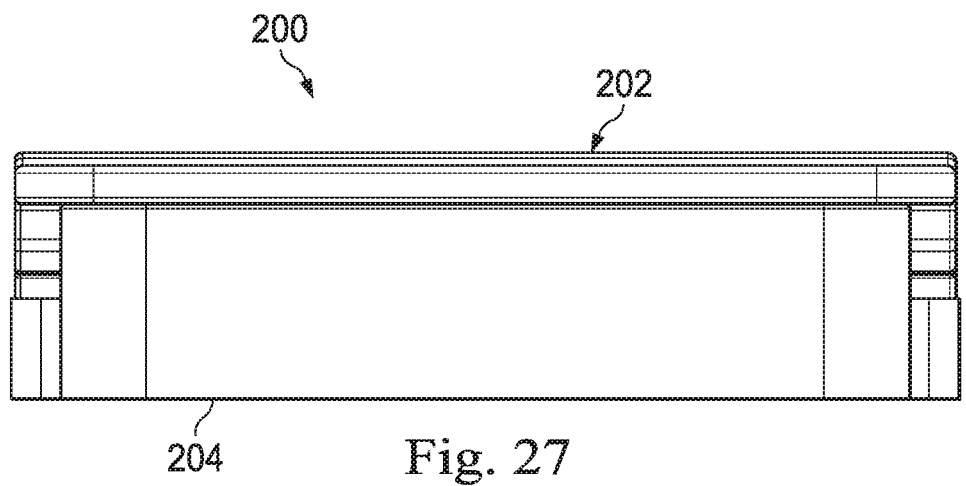
FIG. 27 is a diagrammatic front view of the connector of FIGS. 15-26.
Figure 28:
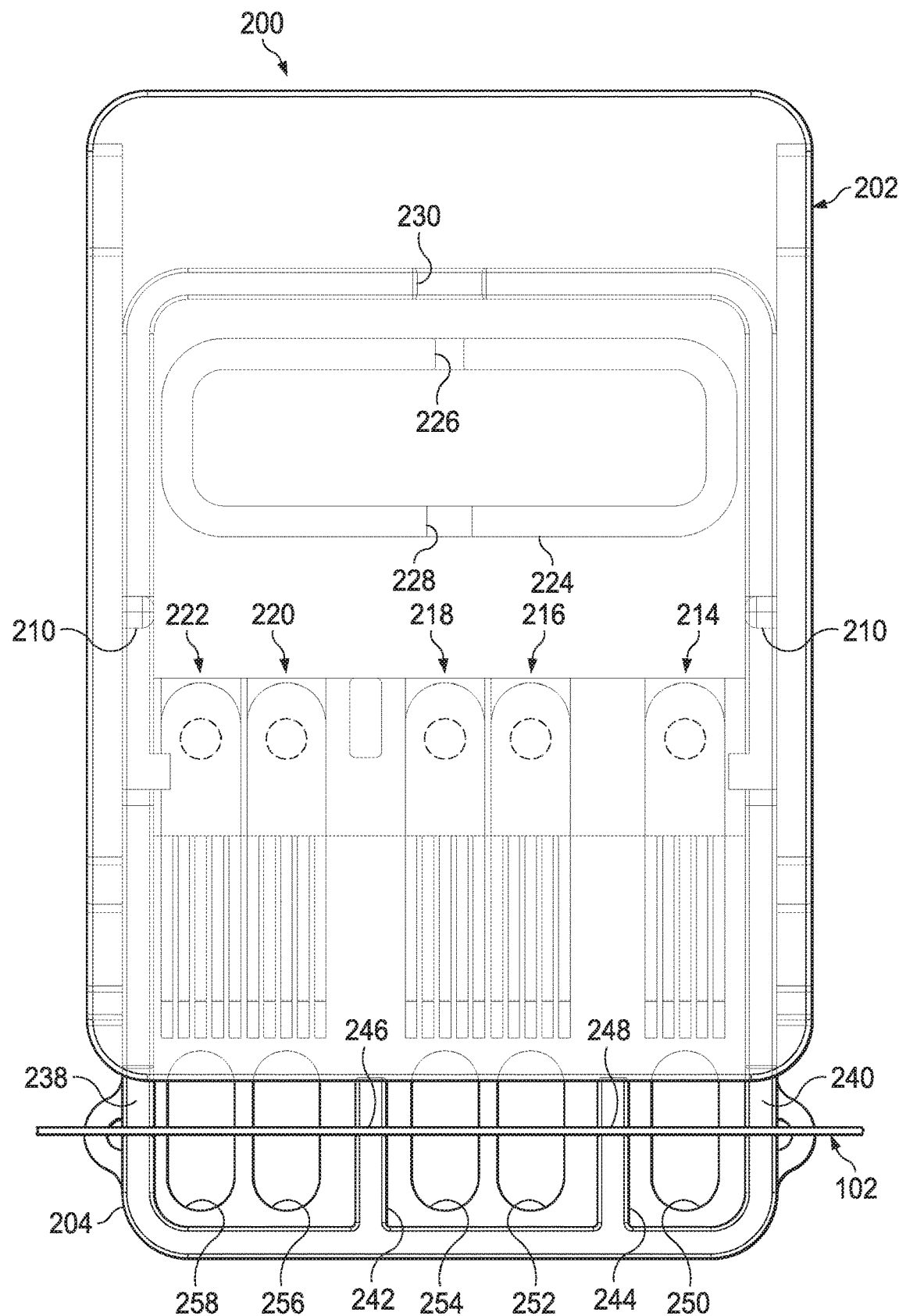
FIG. 28 is a diagrammatic perspective front view of the connector of FIGS. 15-27 shown in an open position and receiving an intravascular device according to an embodiment of the present disclosure.
Figure 29:
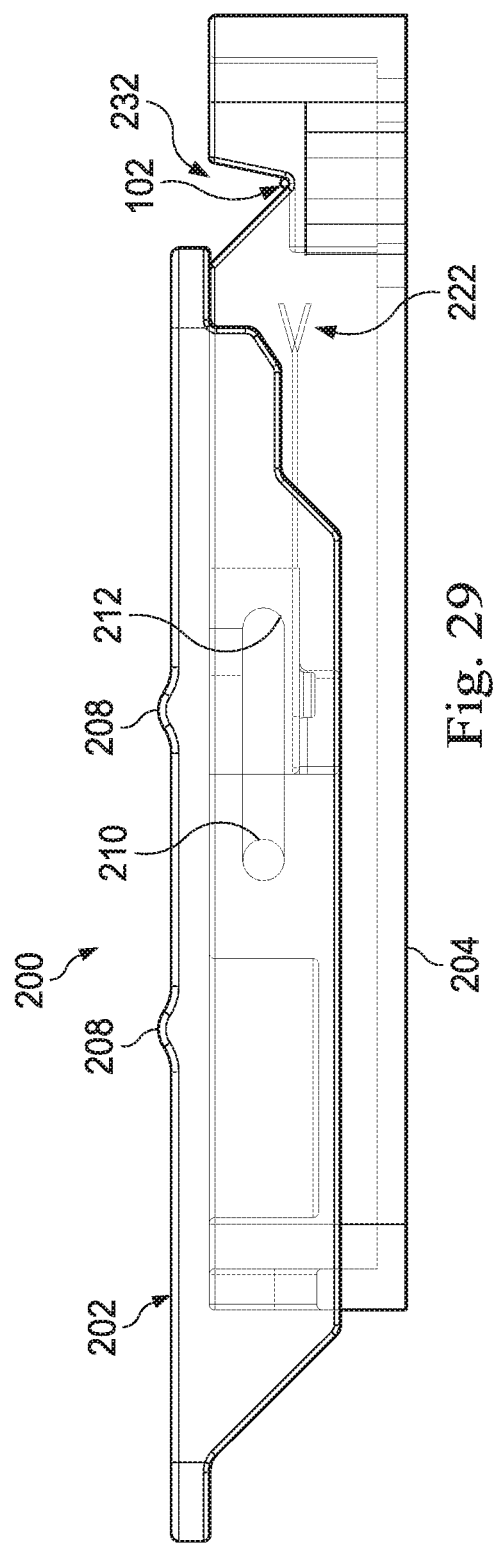
FIG. 29 is a diagrammatic side view of the connector of FIGS. 15-28 in the open position and receiving the intravascular device.
Figure 31:
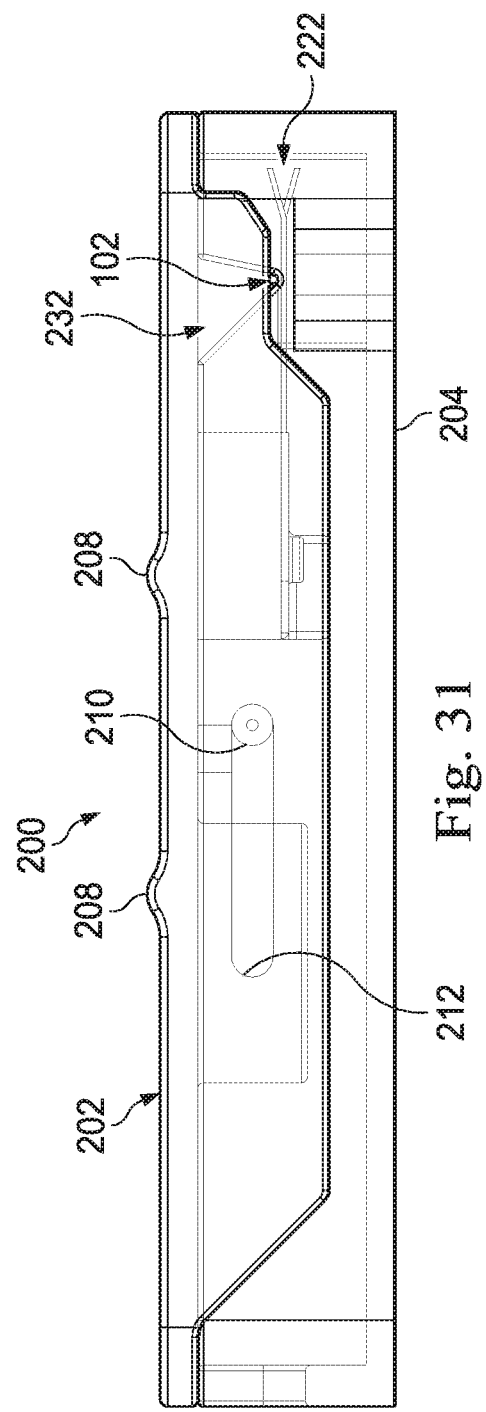
FIG. 31 is a diagrammatic side view of the connector of FIGS. 15-31 in the closed position and receiving the intravascular device.
Figure 30:
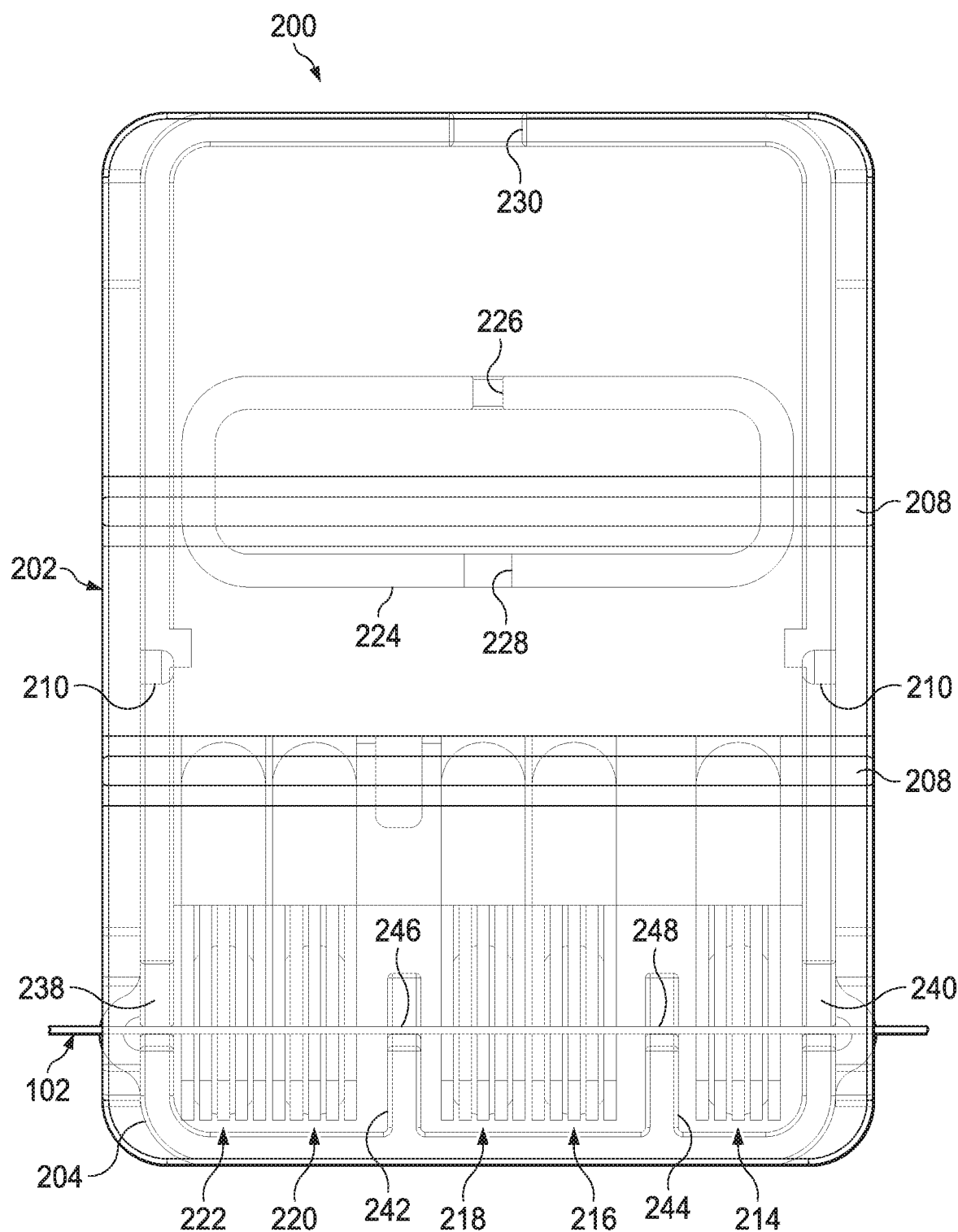
FIG. 30 is a diagrammatic perspective front view of the connector of FIGS. 15-29 shown in a closed position and receiving an intravascular device according to an embodiment of the present disclosure.

Referring now to FIGS. 15-31, shown therein is a connector 200 according to another embodiment of the present disclosure. In that regard, FIG. 15 is a diagrammatic perspective front view of the connector 200; FIG. 16 is a diagrammatic perspective rear view of the connector 200; FIG. 17 is a diagrammatic perspective rear view of the connector 200 similar to that of FIG. 16, but with inner components of the connector 200 illustrated; FIG. 18 is a diagrammatic top view of the connector 200; FIG. 19 is a diagrammatic top view of the connector 200 similar to that of FIG. 18, but with the inner components of the connector 200 illustrated; FIG. 20 is a diagrammatic bottom view of the connector 200; FIG. 21 is a diagrammatic bottom view of the connector 200 similar to that of FIG. 20, but with the inner components of the connector 200 illustrated; FIG. 22 is a diagrammatic side view of the connector 200; FIG. 23 is a diagrammatic side view of the connector 200 similar to that of FIG. 22, but with inner components of the connector 200 illustrated; FIG. 24 is a diagrammatic side view of the connector 200 similar to that of FIG. 22, but from the opposite side of the connector 200; FIG. 25 is a diagrammatic side view of the connector 200 similar to that of FIG. 24, but with inner components of the connector 200 illustrated; FIG. 26 is a diagrammatic rear view of the connector 200; FIG. 27 is a diagrammatic front view of the connector 200; FIG. 28 is a diagrammatic perspective front view of the connector 200 shown in an open position and receiving an intravascular device; FIG. 29 is a diagrammatic side view of the connector 200 in the open position and receiving the intravascular device; FIG. 30 is a diagrammatic perspective front view of the connector 200 shown in a closed position and receiving an intravascular device; and FIG. 31 is a diagrammatic side view of the connector 200 in the closed position and receiving the intravascular device.

As shown in FIG. 15, the connector 200 includes an upper component 202 and a lower component 204. As discussed below, the upper and lower components 202 and 204 are slidable with respect to one another to facilitate insertion of an intravascular device into the connector 200 and subsequent engagement of the connector with the received intravascular device that results in one or more electrical connections between the intravascular device and the connector.

In the illustrated embodiment, the upper component 202 includes an upper surface 206 with gripping features 208 extending therefrom. In that regard, the gripping features 208 are generally representative of any type of structure (e.g., projection(s), recess(es), combinations thereof, etc.), texture (e.g., roughened, knurled, patterned, combinations thereof, etc.) and/or combinations thereof configured to provide an interface to assist a user in translating the upper component 202 relative to the lower component 204. In the illustrated embodiment, the gripping features 208 are rounded projections extending upward from the upper surface 206 of the upper component 202, as shown in FIG. 24. Further, the gripping features 208 extend across a width of the upper component 202 in a direction that is transverse to the longitudinal axis of the upper component 202, as shown in each of FIGS. 15-19. As discussed below, the upper component 202 is configured to translate with respect to the lower component 204 along (or parallel to) the longitudinal axis of the upper component between open and closed positions such that the connector 200 is configured to receive the connection portion of an intravascular device, such as connection portion 114 of intravascular device 102, in a direction that is transverse to the longitudinal axis of the intravascular device. In that regard, the gripping features 208 extend parallel to the longitudinal axis of the intravascular device when the intravascular device is received within and engaged with the connector 200. In some embodiments, the lower component 204 includes one or more gripping features similar to gripping features 208 of upper component 202. In that regard, the lower component 204 may have the same, fewer, or more gripping features than the upper component 202, in the same or a different arrangement, and/or with the same or different structural profiles.

To guide the movement of the upper component 202 with respect to the lower component 204, the upper component 202 includes projections 210 that are received within corresponding slots or openings 212 of the lower component, as best seen in FIGS. 17, 23, 25, 29, and 31. In that regard, the openings 212 are formed in the outer side surfaces of the lower component 204 and extend along the length of the lower component in a direction parallel to the longitudinal axis of the lower component. The projections 210 extend inwardly from an inner side surface of the upper component 202 such that when the upper and lower components 202, 204 are assembled together the projections 210 are received within the openings 212. The projections 210 are sized and shaped to be slidably received within the openings 212 such that the projections 210 can translate along the length of the openings 212 when the upper component 202 is translated relative to the lower component 204. In some instances, the opposing ends of the openings 212 serve as stops to limit travel of the upper component 202 relative to the lower component 204. In that regard, the projection 210 will contact a first end of the opening when the upper component 202 is in the fully opened position (See, e.g., FIG. 29) and will contact a second end of the opening opposite the first end when the upper component is in the fully closed position (See, e.g., FIG. 31). In some embodiments, the connector 200 includes a spring detent to lightly lock the mechanism in the closed position. In that regard, the spring detent biases the upper component 202 of the connector 200 toward the closed position through at least part of the sliding motion between the upper and lower components.

As shown in FIGS. 17, 19, 21, 23, 25, and 28-31, the upper component 202 includes electrical contacts 214, 216, 218, 220, and 222. In that regard, the electrical contacts 214, 216, 218, 220, and 222 are configured to engage corresponding electrical contacts of an intravascular device, such as conductive portions 122, 124, and 126 of connection portion 114 of the intravascular device 102. For example, in the illustrated embodiment electrical contact 214 is configured to be electrically coupled to conductive portion 122, electrical contacts 216 and 218 are configured to be electrically coupled to conductive portion 124, and electrical contacts 220 and 222 are configured to be electrically coupled to conductive portion 126. It is understood, however, that any arrangement of electrical connection between the connector 200 and an intravascular device may be utilized. In that regard, the connector 200 may include any number of electrical contacts (e.g., 1, 2, 3, 4, 5, 6, 7, 8, or more electrical contacts), may include a single contact for each of one or more conductive portions of the intravascular device, may include multiple contacts for each of one or more conductive portions of the intravascular device, and/or combinations thereof. Further, in the illustrated embodiment the electrical contacts 214, 216, 218, 220, and 222 are split, open-comb electrical contacts. In that regard, each of the electrical contacts 214, 216, 218, 220, and 222 is configured to receive a conductive portion of an intravascular device therein such that some of the teeth of the open-comb electrical contact will be positioned above the conductive portion and others of the teeth of the open-comb electrical contact will be positioned below the conductive portion. This arrangement provides a secure and reliable electrical connection between the electrical contact of the connector 200 and the corresponding conductive portion of the intravascular device. Further, as discussed below with respect to FIGS. 28-31, the open-comb electrical contacts are particularly well-suited to facilitate proper electrical connection between the connector 200 and an intravascular device positioned within the lower component 204 when the upper component 202 is translated relative to the lower component 204 from the open position towards the closed position. Further, the open-comb configuration allows for the intravascular device to be rotated with respect to the connector while maintaining a proper connection. Thus, the open-comb configuration allows a user (e.g., surgeon) to keep the connector 200 connected to the intravascular device while the intravascular device is moved or advanced through the vasculature with little resistance to rotational movement of the intravascular device. In other words, the intravascular device can be moved through the vascular, undergoing various twists and turns, without the connector 200 needing to move with rotations of the intravascular device. Also, the open-comb configuration helps ensure good electrical contact due to the multiple fingers for each of the contacts. In addition, the open end of the open-comb configuration provides a good guide for ensuring that the intravascular device is correctly positioned when the upper component is closed onto the intravascular. While various advantages of the open-comb configuration have been described, it is understood that any appropriately sized electrical contacts can be utilized, including a single contact or a plurality of contacts.

Similar to the connectors 104 and 170 discussed above, the connector 200 is configured to interface with a connection portion of an intravascular device to facilitate communication between the intravascular device and a separate component. In particular, the connector 200 is configured to facilitate communication between one or more electronic components of the intravascular device (that are electrically coupled to the connection portion) and a separate component, such as a processing system associated with the one or more electronic components. To that end, the connector 200 includes a communication cable (not shown) that is configured to carry signals between the connector 200 and the separate component. In particular, the cable is configured to carry electrical signals and includes one or more electrical conductors extending along its length to facilitate such electrical communication. However, the type of communication cable utilized is dependent on the type of electronic, optical, and/or electro-optical components that are incorporated into the intravascular device. In that regard, the communication cable may include one or more of an electrical conductor, an optical fiber, and/or combinations thereof. In some instances, the cable is configured to be plugged into an interface of a processing system. In that regard, the interface is a patient interface module (PIM) in some instances.

As best shown in FIGS. 17 and 19, the upper component 202 includes a support structure 224 that has openings 226 and 228 extending therethrough that facilitate passage of the cable therethrough. In particular, the openings 226 and 228 are configured to allow the cable to extend through the upper component 202 from the coupling of the electrical conductors of the cable to the electrical contacts 214, 216, 218, 220, and 222. In some instances, the electrical conductors of the cable are soldered to the electrical contacts 214, 216, 218, 220, and 222 of the upper connection piece. The openings 226 and 228 are generally aligned with an opening 230 of the lower component 204. In that regard, the cable extends through opening 230 in some embodiments. The arrangement of the openings 226, 228, and 230 allows the upper component 202 to translate with respect to the lower component 204 without damaging the electrical couplings between the electrical conductors of the cable and the electrical contacts 214, 216, 218, 220, and 222 of the upper component and without creating unwanted kinking/bending of the cable. While in the illustrated embodiment, the electrical contacts 214, 216, 218, 220, and 222 are fixedly secured to the upper component 202, in other embodiments, the electrical contacts are fixedly secured to the lower component 204 and the lower component includes necessary recesses, openings, and/or passages to facilitate connection of the communication cable to the contacts and passing of the cable out of the connector.

As best shown in FIGS. 23, 25, 29, and 31, the lower component 204 includes a recess 232 that is sized and shaped to receive an intravascular device. In particular, the recess 232 is sized and shaped to receive a connection portion of the intravascular device. In the illustrated embodiment, the width of the recess 232 tapers from wider to narrower as the recess extends into the lower component 204. In that regard, the recess 232 includes a surface 234 and an opposing surface 236 that generally define the recess 232. The recess 232 is configured to maintain the connection portion of the intravascular device in position within the connector 200. In particular, the surface 236 is configured to maintain the intravascular device within the recess 232 as the upper component 202 is advanced relative to the lower component 204 and into engagement with the intravascular device. Accordingly, in some embodiments the surface 236 extends generally perpendicular to the longitudinal axis of the lower component to prevent the intravascular device from sliding up surface 236 and out of the recess 232 as the electrical contacts of the upper component 202 are advanced into electrical engagement with the intravascular device. In some particular embodiments, the surface 236 extends at an angle between about 60 degrees and about 120 degrees relative to the longitudinal axis of the lower component 204. In other embodiments, the surface 236 extends at an angle outside of this range (either smaller or larger). In the illustrated embodiment, the surface 236 extends at an angle of about 85 degrees relative to the longitudinal axis of the lower component, while the surface 234 extends at an angle of about 135 degrees relative to the longitudinal axis of the lower component (See, e.g., FIG. 23).

In some embodiments, such as the illustrated embodiment, the recess 232 has discontinuities as it extends across the width of the lower component. In particular, as shown in FIG. 28 of the illustrated embodiment, the lower component 204 includes outer portions 238 and 240 that define the outer boundaries of the recess 232. The outer portions 238 and 240 include surfaces 234 and 236 as discussed above. Further, the lower component 204 also includes supports 242, 244 having recess portions 246, 248, respectively. In that regard, the recess portions 246 and 248 are portions of recess 232 and are configured to receive the intravascular device. In some embodiments, the recess portions 246 and 248 include tapered surfaces similar to surfaces 234 and 236 discussed above. However, in other embodiments the recess portions 246 and 248 comprise only the bottom portion of the recess 232 that is sized and shaped to receive the intravascular device. For example, as shown in FIGS. 28 and 30, the recess portion 246 and 248 have a maximum length along the longitudinal axis of the lower component 204 that is much smaller than the maximum length of the recess 232 at the outer portions 238 and 240. It is understood that, in other embodiments, the arrangement of the recess 232 as defined by outer portions 238, 240 is similar to that defined by supports 242, 244 and/or vice versa.

To help ensure that the connection portion of the intravascular device is properly aligned with the electrical contacts of the connector 200, the upper and/or lower component(s) 202, 204 may include one or more visual markers (active and/or passive) and/or be at least partially formed of a clear or translucent material as discussed above with respect to connectors 104 and 170. Further, in the illustrated embodiment, the lower component 204 includes openings 250, 252, 254, 256, and 258 that extend through the lower surface of the lower component in general alignment with where the conductive portions of the intravascular device should be positioned when received by the connector 200. Accordingly, in some instances a user can look through the opening to confirm proper positioning of the intravascular device within the connector 200. For example, when intravascular device 102 is utilized with connector 200, conductive portion 120 can be visualized through opening 250, conductive portion 122 can be visualized through at least one of openings 252 and 254, and conductive portion 124 can be visualized through at least one of openings 256 and 258.

Referring more specifically to FIGS. 28-31, shown therein is a transition of the connector 200 from the open positioned to the closed position. In that regard, the connector 200 is shown in the open position in FIGS. 28 and 29. As shown, the connector 200 is configured to receive the intravascular device 102 in a side-loading fashion. More specifically, the recess 232 in the lower component 204 is revealed when the upper component 202 is retracted to the open position such that the intravascular device 102 can be seated within the recess by moving the intravascular device 102 in a direction transverse to its longitudinal axis. To load the intravascular device within the connector 200, the connector 200 may be moved relative to the intravascular device 102, the intravascular device 102 may be moved relative to the connector 200, and/or combinations thereof. With the intravascular device 102 positioned within the recess 232 of the lower component, the upper component 202 is translated with respect to the lower component 204 by projections 210 sliding along guide slots 212 to the closed position illustrated in FIGS. 30 and 31. In the closed position, the intravascular device 102 is held between the upper and lower components 202 and 204 such that the connector 200 is in electrical communication with the connection portion 114 of the intravascular device. In particular, as the upper component 202 is advanced towards the closed position the split teeth of the open-comb electrical contacts 214, 216, 218, 220, and 222 engage the connection portion 114 of the intravascular device 102. In that regard, the bottom of the recess 232 is positioned relative to the electrical contacts 214, 216, 218, 220, and 222 such that the intravascular device will be aligned with the electrical contacts 214, 216, 218, 220, and 222 in the vertical direction when the intravascular device is seated within the recess. Accordingly, with the intravascular device 102 seated in the recess such that the conductive portions 120, 122, and 124 of the connection portion 114 are aligned both horizontally and vertically with respect to the electrical contacts of the connector 200, advancement of the upper component 202 to the closed position electrically couples the connector 200 to the intravascular device 102.

Figure 32:
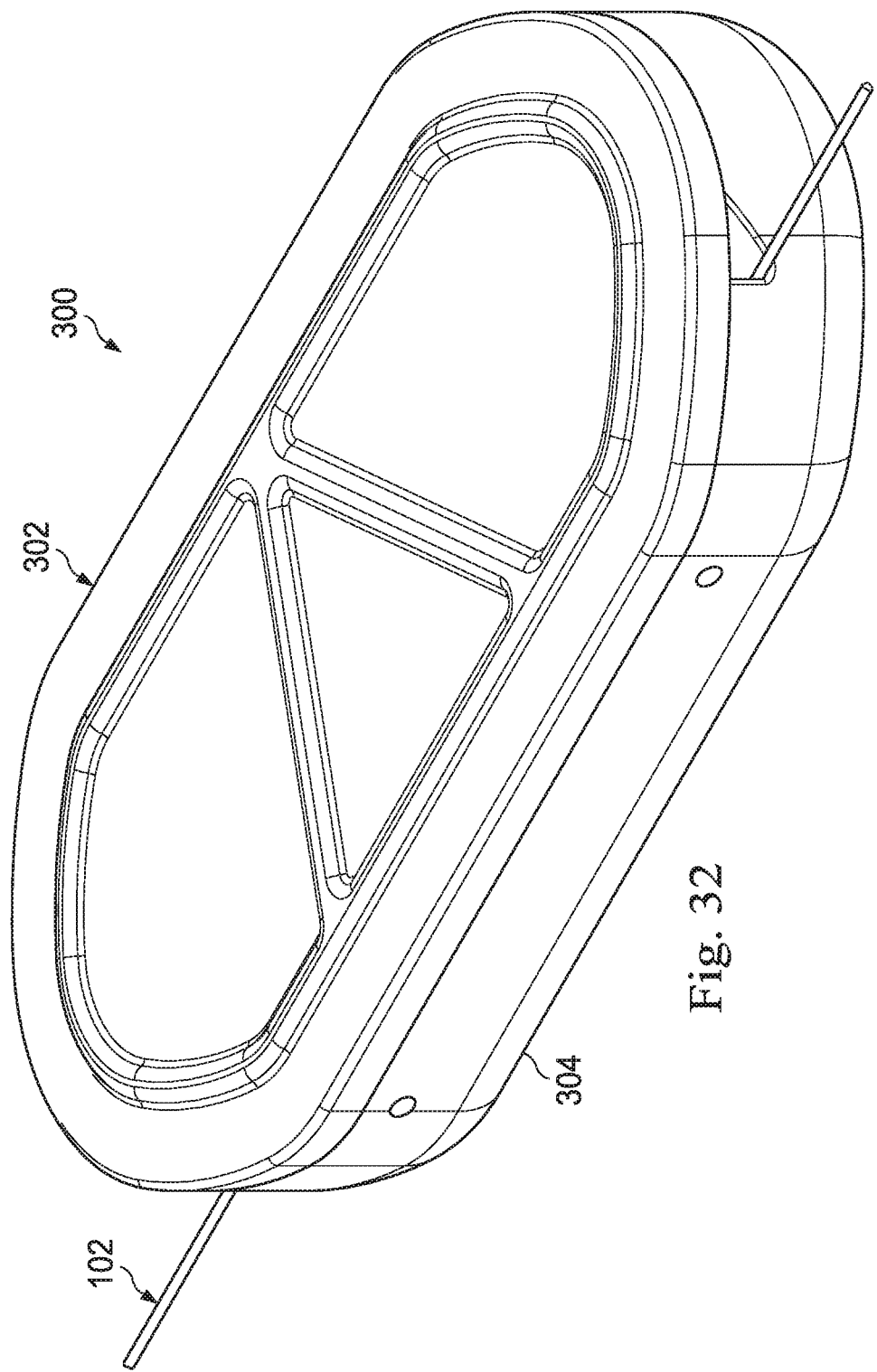
FIG. 32 is a diagrammatic perspective front view of a connector of the intravascular system of FIG. 1 according to yet another embodiment of the present disclosure.
Figure 33:
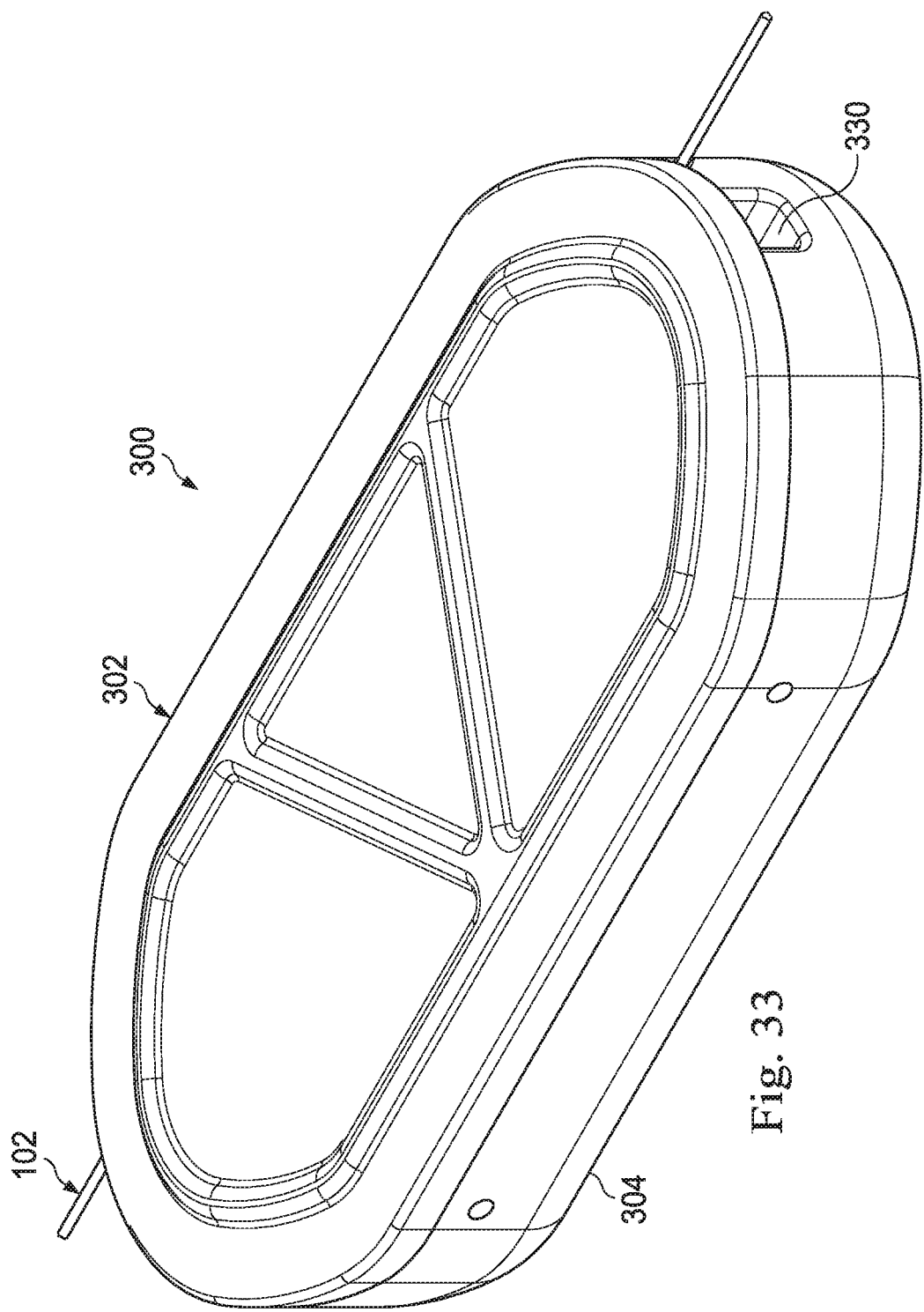
FIG. 33 is a diagrammatic perspective rear view of the connector of FIG. 32.
Figure 34:
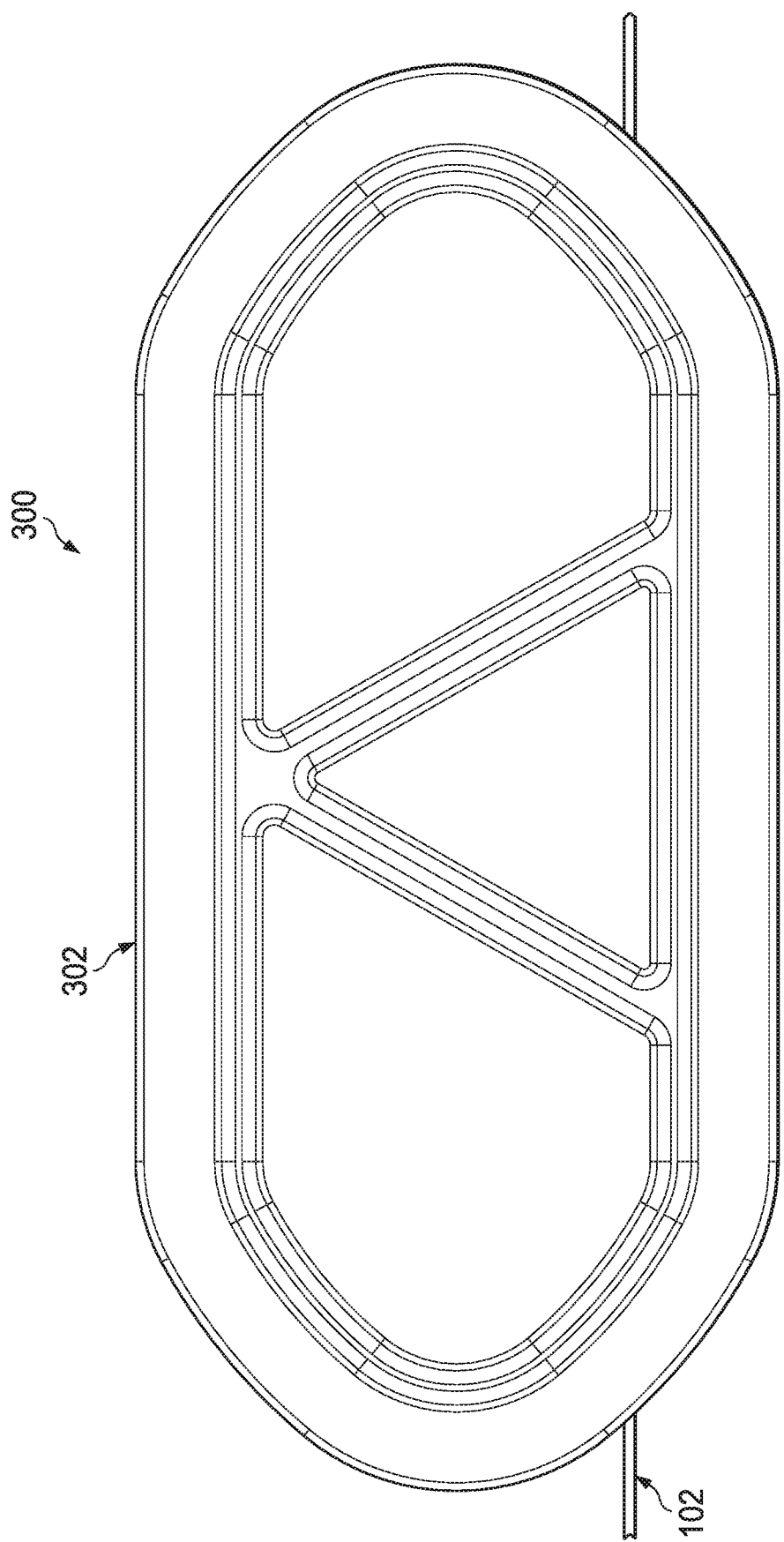
FIG. 34 is a diagrammatic top view of the connector of FIGS. 32 and 33.
Figure 35:
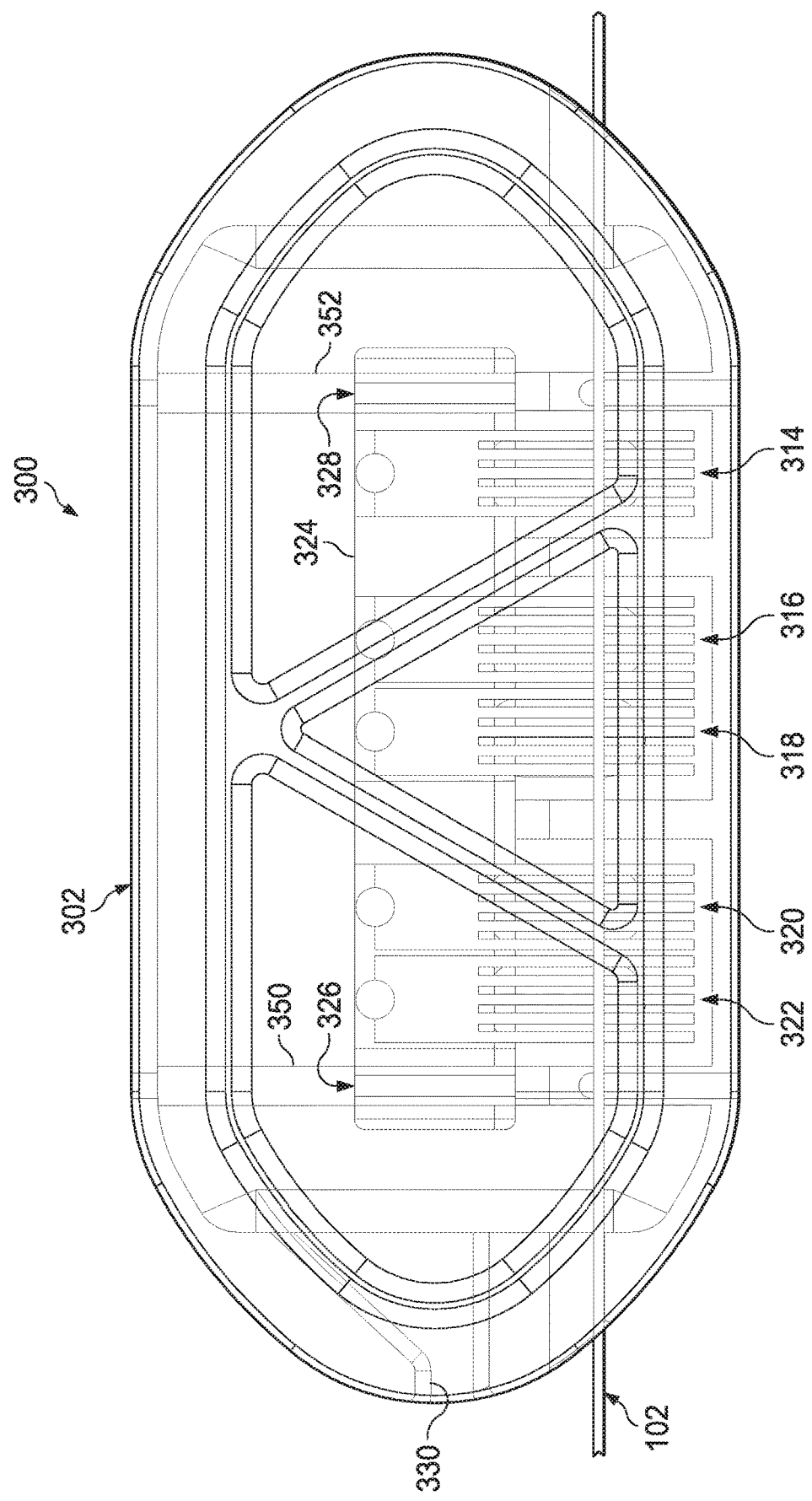
FIG. 35 is a diagrammatic top view of the connector similar to that of FIG. 34, but with the inner components of the connector illustrated.
Figure 36:
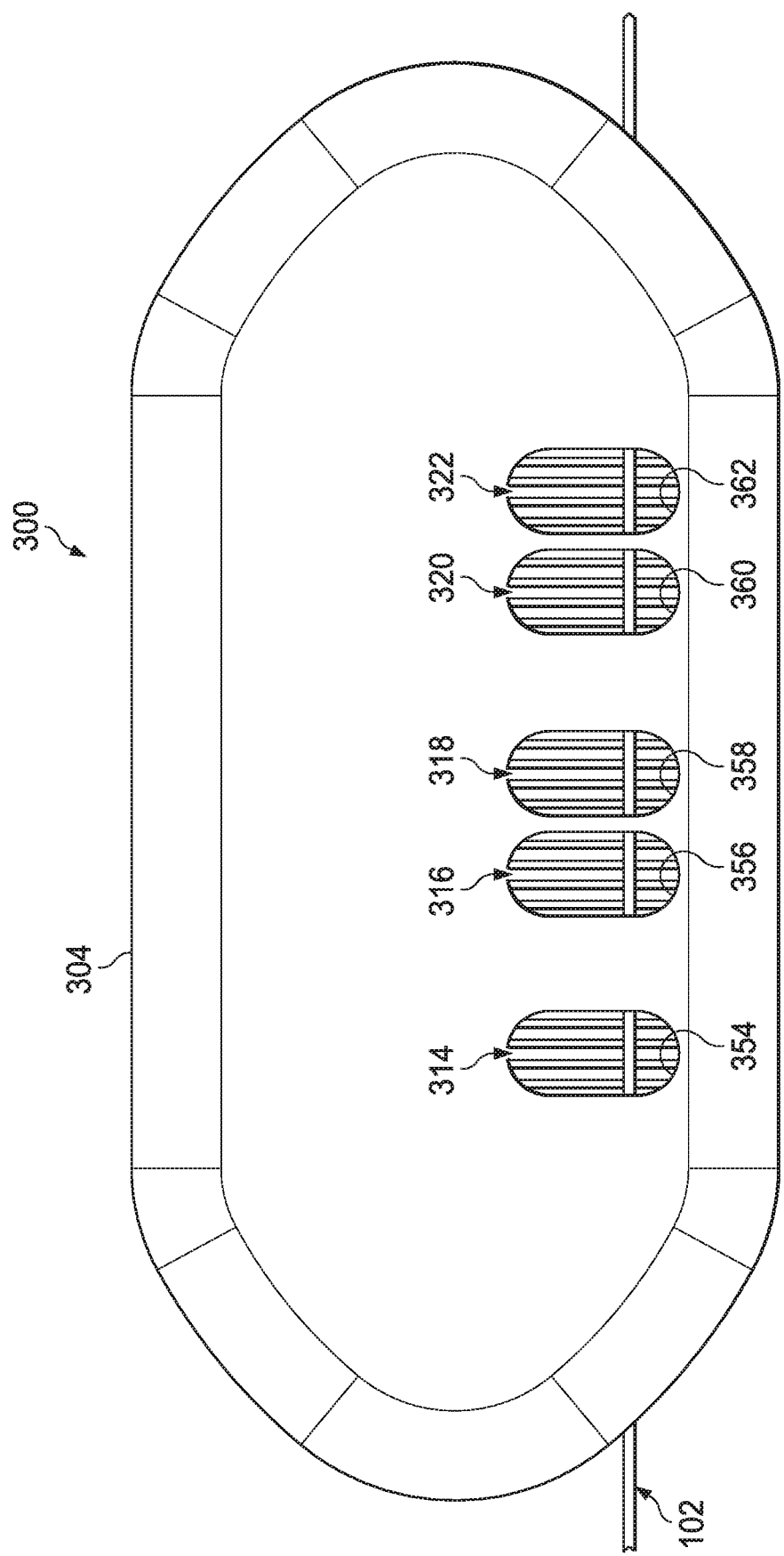
FIG. 36 is a diagrammatic bottom view of the connector of FIGS. 32-35.
Figure 37:
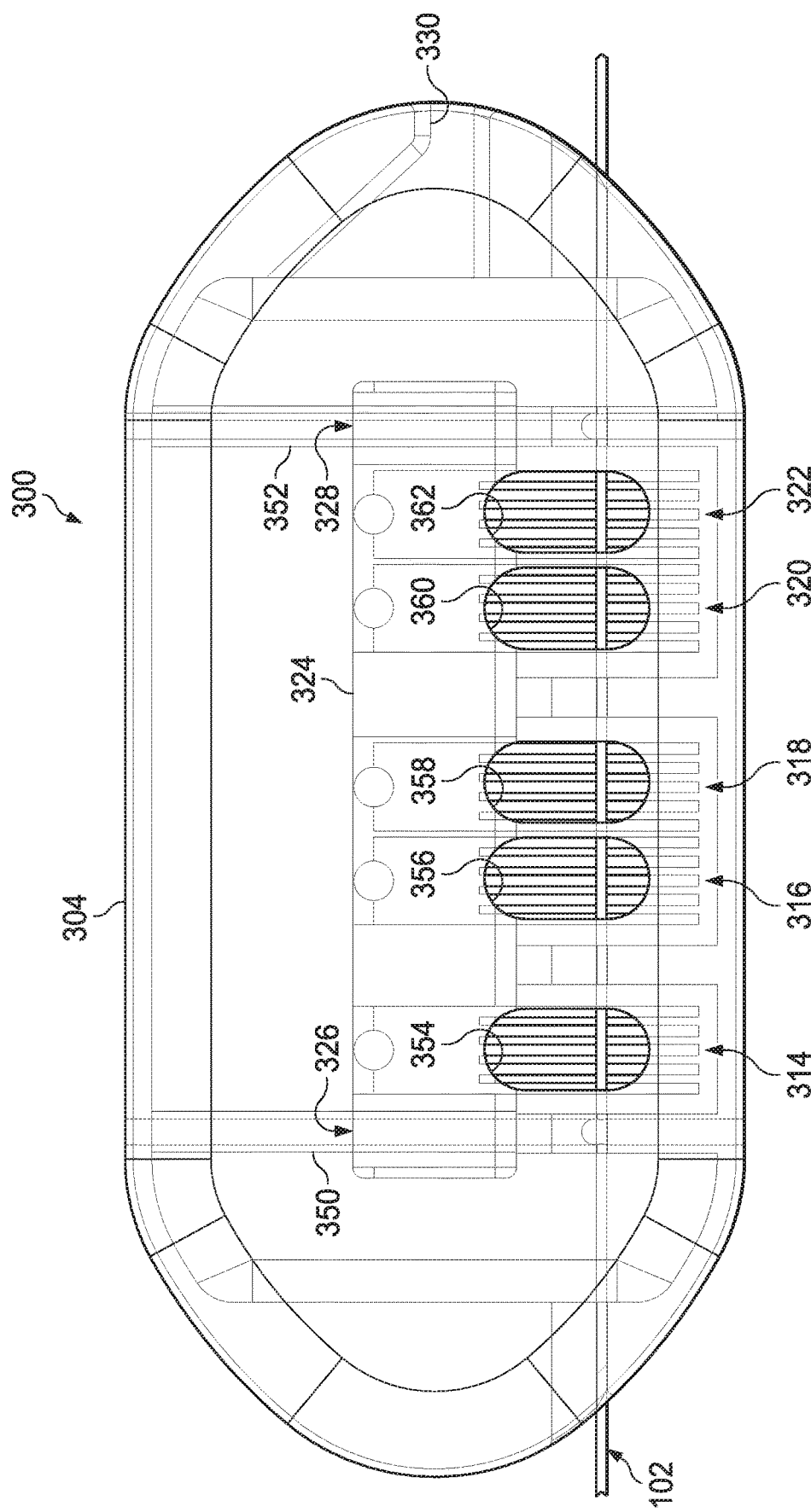
FIG. 37 is a diagrammatic bottom view of the connector similar to that of FIG. 36, but with the inner components of the connector illustrated.
Figure 38:
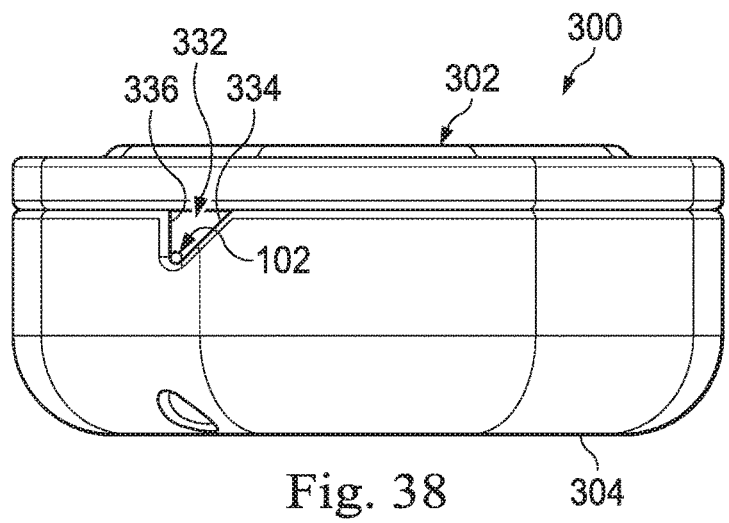
FIG. 38 is a diagrammatic side view of the connector of FIGS. 32-37.
Figure 39:
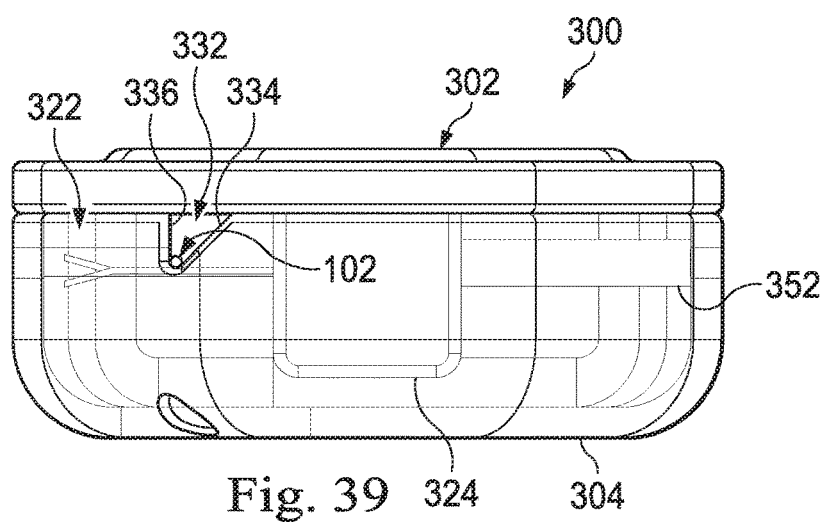
FIG. 39 is a diagrammatic side view of the connector similar to that of FIG. 38, but with inner components of the connector illustrated.
Figure 40:
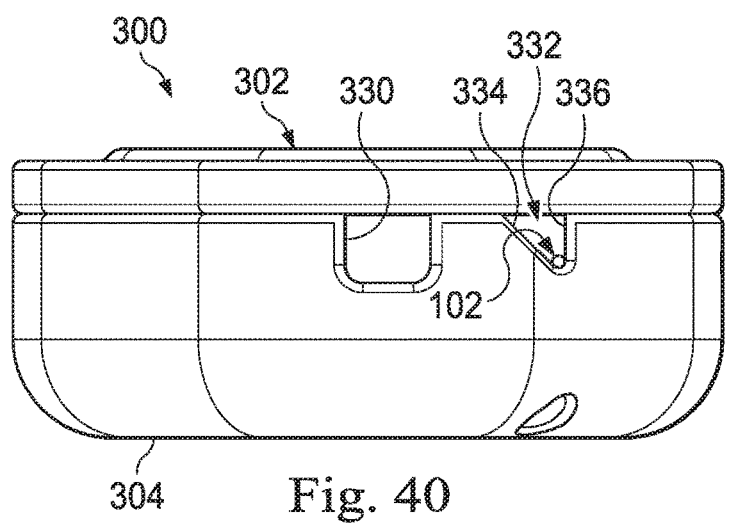
FIG. 40 is a diagrammatic side view of the connector of FIGS. 32-39 similar to that of FIG. 38, but from the opposite side of the connector.
Figure 41:
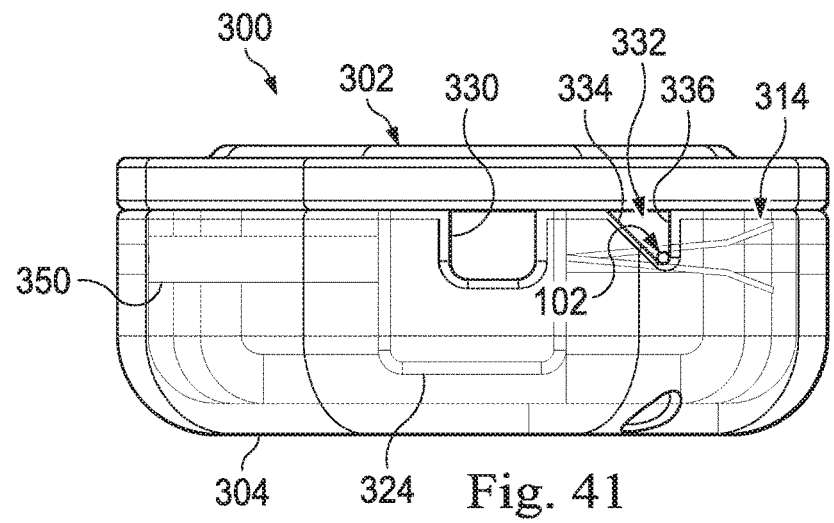
FIG. 41 is a diagrammatic side view of the connector similar to that of FIG. 40, but with inner components of the connector illustrated.
Figure 45:
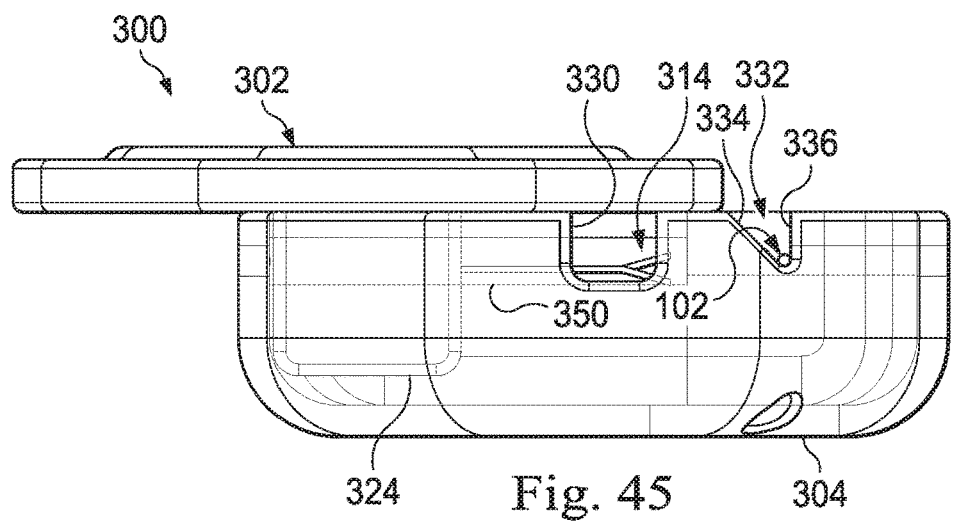
FIG. 45 is a diagrammatic side view of the connector of FIGS. 32-44 in the open position and receiving the intravascular device.
Figure 47:
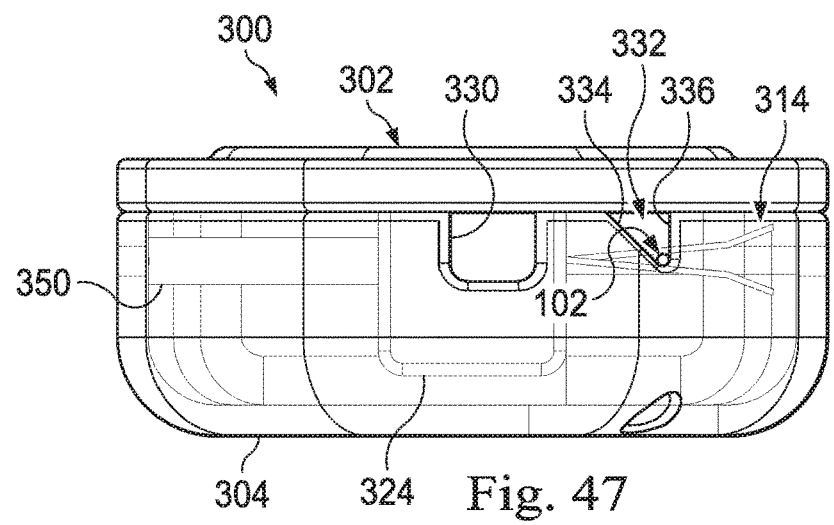
FIG. 47 is a diagrammatic side view of the connector of FIGS. 32-46 in the closed position and receiving the intravascular device.
Figure 44:
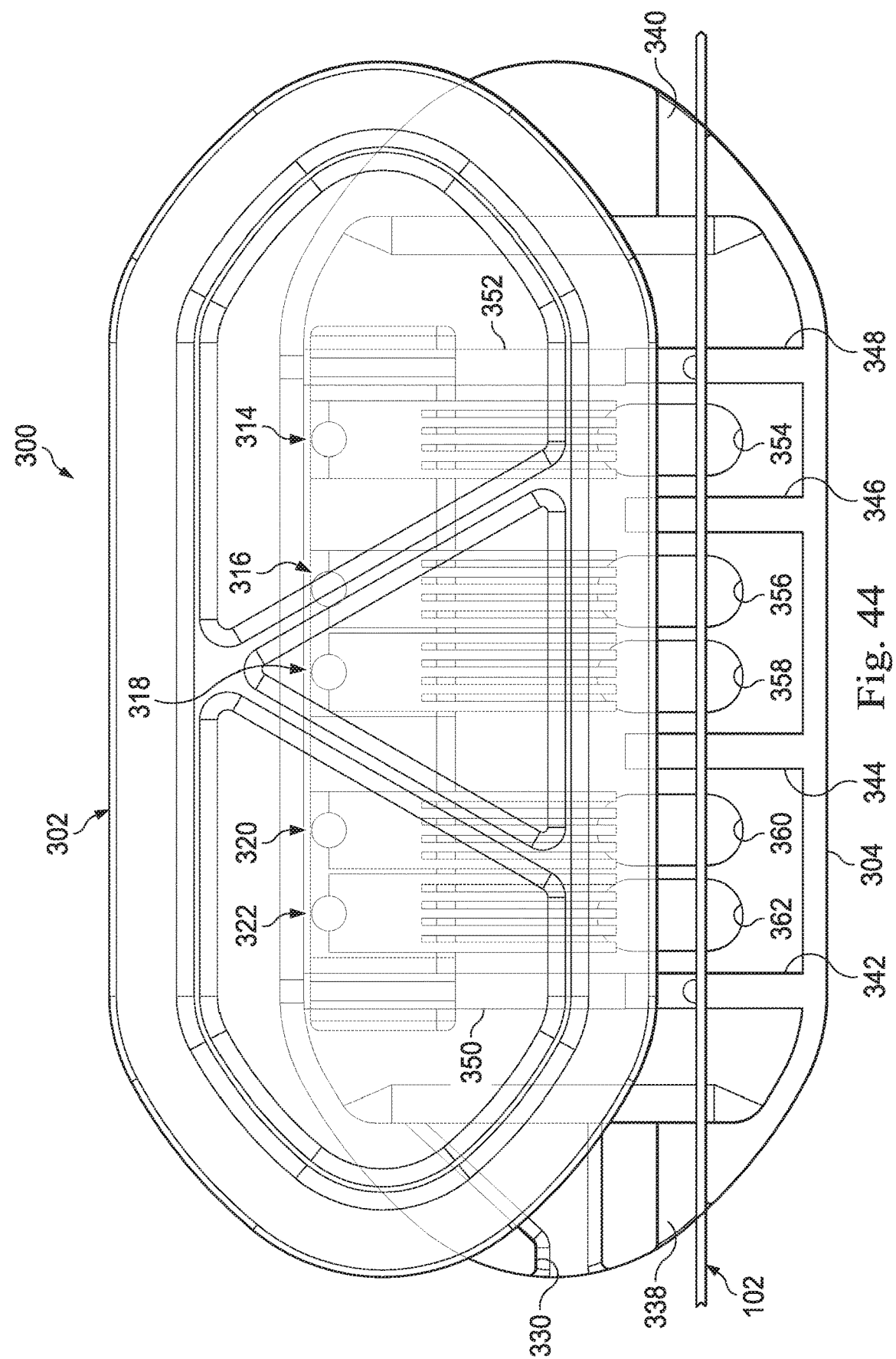
FIG. 44 is a diagrammatic top view of the connector of FIGS. 32-43 shown in an open position and receiving an intravascular device according to an embodiment of the present disclosure.
Figure 46:
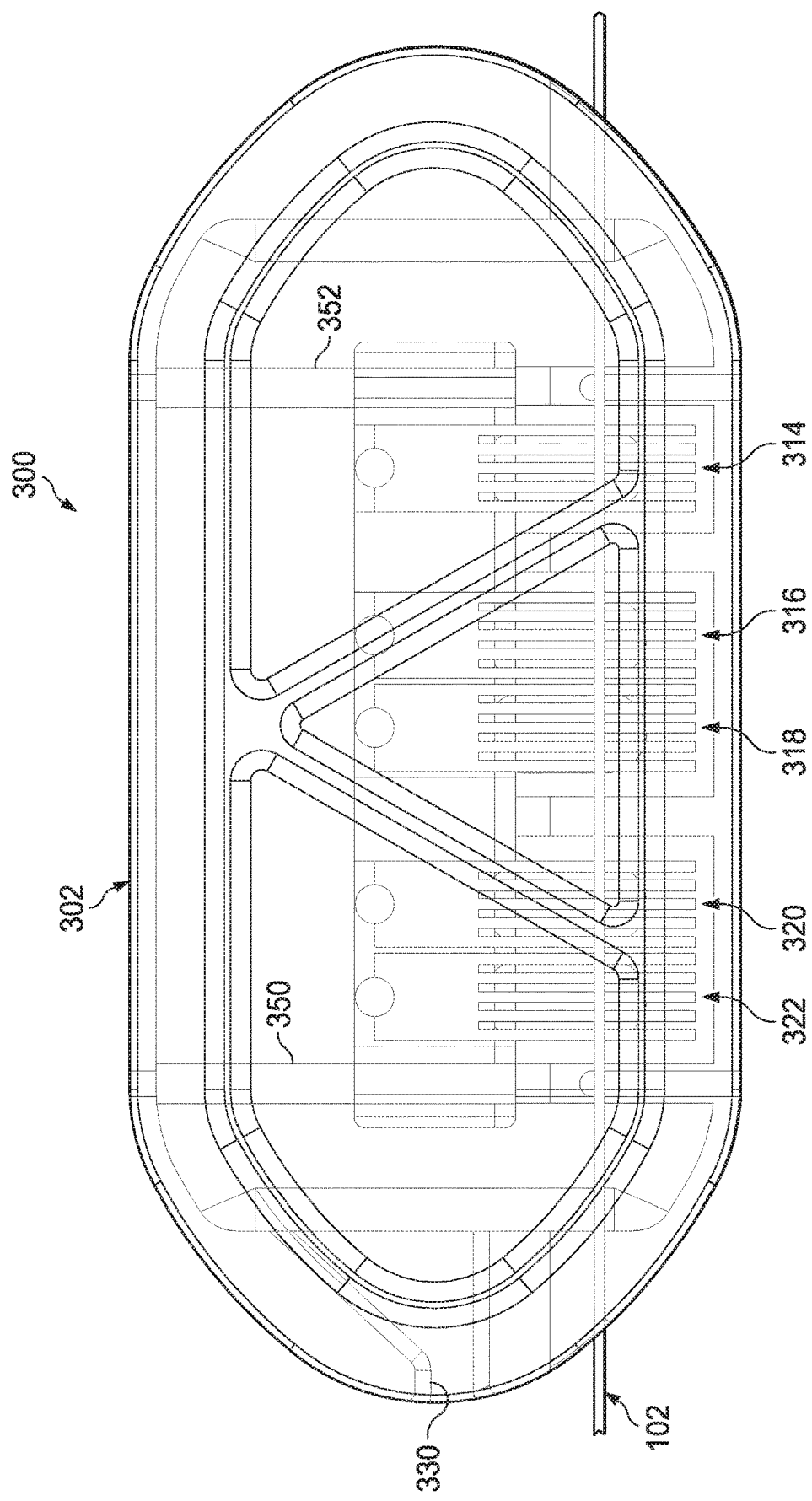
FIG. 46 is a diagrammatic perspective front view of the connector of FIGS. 32-45 shown in a closed position and receiving an intravascular device according to an embodiment of the present disclosure.

Referring now to FIGS. 32-47, shown therein is a connector 300 according to another embodiment of the present disclosure. In that regard, FIG. 32 is a diagrammatic perspective front view of the connector 300; FIG. 33 is a diagrammatic perspective rear view of the connector 300; FIG. 34 is a diagrammatic top view of the connector 300; FIG. 35 is a diagrammatic top view of the connector 300 similar to that of FIG. 34, but with the inner components of the connector 300 illustrated; FIG. 36 is a diagrammatic bottom view of the connector 300; FIG. 37 is a diagrammatic bottom view of the connector 300 similar to that of FIG. 36, but with the inner components of the connector 300 illustrated; FIG. 38 is a diagrammatic side view of the connector 300; FIG. 39 is a diagrammatic side view of the connector 300 similar to that of FIG. 38, but with inner components of the connector 300 illustrated; FIG. 40 is a diagrammatic side view of the connector 300 similar to that of FIG. 38, but from the opposite side of the connector 300; FIG. 41 is a diagrammatic side view of the connector 300 similar to that of FIG. 40, but with inner components of the connector 300 illustrated; FIG. 42 is a diagrammatic rear view of the connector 300; FIG. 43 is a diagrammatic rear view of the connector similar to that of FIG. 42, but with inner components of the connector illustrated; FIG. 44 is a diagrammatic top view of the connector 300 shown in an open position and receiving an intravascular device; FIG. 45 is a diagrammatic side view of the connector 300 in the open position and receiving the intravascular device; FIG. 46 is a diagrammatic perspective front view of the connector 300 in a closed position and receiving an intravascular device; and FIG. 47 is a diagrammatic side view of the connector 300 in the closed position and receiving the intravascular device.

As shown in FIG. 32, the connector 300 includes an upper component 302 and a lower component 304. As discussed below, the upper and lower components 302 and 304 are slidable with respect to one another to facilitate insertion of an intravascular device into the connector 300 and subsequent engagement of the connector with the received intravascular device that results in one or more electrical connections between the intravascular device and the connector. In that regard, the upper component 302 includes electrical contacts 314, 316, 318, 320, and 322, as shown in FIGS. 35-37, 39, 41, and 44-47. The electrical contacts 314, 316, 318, 320, and 322 are configured to engage corresponding electrical contacts of an intravascular device, such as conductive portions 122, 124, and 126 of connection portion 114 of the intravascular device 102. For example, in the illustrated embodiment electrical contact 314 is configured to be electrically coupled to conductive portion 122, electrical contacts 316 and 318 are configured to be electrically coupled to conductive portion 124, and electrical contacts 320 and 322 are configured to be electrically coupled to conductive portion 126. It is understood, however, that any arrangement of electrical connection between the connector 200 and an intravascular device may be utilized. In that regard, the connector 200 may include any number of electrical contacts (e.g., 1, 2, 3, 4, 5, 6, 7, 8, or more electrical contacts), may include a single contact for each of one or more conductive portions of the intravascular device, may include multiple contacts for each of one or more conductive portions of the intravascular device, and/or combinations thereof. Further, in the illustrated embodiment the electrical contacts 314, 316, 318, 320, and 322 are split, open-comb electrical contacts. In that regard, each of the electrical contacts 314, 316, 318, 320, and 322 is configured to receive a conductive portion of an intravascular device therein such that some of the teeth of the open-comb electrical contact will be positioned above the conductive portion and others of the teeth of the open-comb electrical contact will be positioned below the conductive portion. This arrangement provides a secure and reliable electrical connection between the electrical contact of the connector 300 and the corresponding conductive portion of the intravascular device. Further, as discussed below with respect to FIGS. 44-47, the open-comb electrical contacts are particularly well-suited to facilitate proper electrical connection between the connector 300 and an intravascular device positioned within the lower component 304 when the upper component 302 is translated relative to the lower component 304 from the open position towards the closed position. However, any appropriately sized electrical contacts can be utilized, including a single contact or a plurality of contacts.

Similar to the connectors 104, 170, and 200 discussed above, the connector 300 is configured to interface with a connection portion of an intravascular device to facilitate communication between the intravascular device and a separate component. In particular, the connector 300 is configured to facilitate communication between one or more electronic components of the intravascular device (that are electrically coupled to the connection portion) and a separate component, such as a processing system associated with the one or more electronic components. To that end, the connector 300 includes a communication cable (not shown) that is configured to carry signals between the connector 300 and the separate component. In particular, the cable is configured to carry electrical signals and includes one or more electrical conductors extending along its length to facilitate such electrical communication. However, the type of communication cable utilized is dependent on the type of electronic, optical, and/or electro-optical components that are incorporated into the intravascular device. In that regard, the communication cable may include one or more of an electrical conductor, an optical fiber, and/or combinations thereof. In some instances, the cable is configured to be plugged into an interface of a processing system. In that regard, the interface is a patient interface module (PIM) in some instances.

The upper and lower components 302 and 304 of the connector 300 are configured to allow the cable to extend from the couplings between the electrical conductors of the cable to the electrical contacts 314, 316, 318, 320, and 322 out through an opening 330 in a side of the lower component 304, as shown in FIGS. 40 and 41 for example. The arrangement of the upper and lower components 302 and 304, including opening 330, allows the upper component 302 to translate with respect to the lower component 304 without damaging the electrical couplings between the electrical conductors of the cable and the electrical contacts 314, 316, 318, 320, and 322 of the upper component and without creating unwanted kinking/bending of the cable. While in the illustrated embodiment, the electrical contacts 314, 316, 318, 320, and 322 are fixedly secured to the upper component 302, in other embodiments, the electrical contacts are fixedly secured to the lower component 304.

As best shown in FIGS. 35, 37, 39, 41, 45, and 47, the upper component 302 includes a structure 324 that has openings 326 and 328 extending therethrough. Further, to facilitate passage of the cable out of the connector 300, the upper component 302 includes an opening 330, as shown, for example, in FIGS. 33, 35, 37, 40, 41, and 44-47. In the illustrated embodiment, the opening 330 extends through an end or side of the connector 300. Accordingly, this configuration allows the cable to come out of the connector 300 in the same direction as an intravascular device received by the connector. This is beneficial in some instances where the user (e.g., surgeon) wants to leave the connector 300 coupled to the intravascular device while performing a procedure. In other embodiments, the opening 330 is positioned elsewhere around the perimeter of the connector 300. As best shown in FIGS. 38-41, 45, and 47, the lower component 304 includes a recess 332 that is sized and shaped to receive an intravascular device. In particular, the recess 332 is sized and shaped to receive a connection portion of the intravascular device. In the illustrated embodiment, the width of the recess 332 tapers from wider to narrower as the recess extends into the lower component 304. In that regard, the recess 332 includes a surface 334 and an opposing surface 336 that generally define the recess 332. The recess 332 is configured to maintain the connection portion of the intravascular device in position within the connector 300. In particular, the surface 336 is configured to maintain the intravascular device within the recess 332 as the upper component 302 is advanced relative to the lower component 304 and into engagement with the intravascular device. Accordingly, in some embodiments the surface 336 extends generally perpendicular to the longitudinal axis of the lower component to prevent the intravascular device from sliding up surface 336 and out of the recess 332 as the electrical contacts of the upper component 302 are advanced into electrical engagement with the intravascular device. In some particular embodiments, the surface 336 extends at an angle between about 60 degrees and about 120 degrees relative to a longitudinal axis of the lower component 304 (e.g., a longitudinal axis extending left-to-right in each of FIGS. 38-41, 45, and 47). In other embodiments, the surface 336 extends at an angle outside of this range (either smaller or larger). In the illustrated embodiment of FIG. 45, for example, the surface 336 extends at an angle of about 85 degrees relative to a longitudinal axis of the lower component extending left-to-right in the drawing, while the surface 334 extends at an angle of about 135 degrees relative to the longitudinal axis of the lower component.

In some embodiments, the recess 332 has discontinuities as it extends across the width of the lower component. For example, as shown in FIG. 44 of the illustrated embodiment, the lower component 304 includes outer portions 338 and 340 that define the outer boundaries of the recess 332. The outer portions 338 and 340 include surfaces 334 and 336 as discussed above. Further, the lower component 304 also includes supports 342, 344, 346, and 348 having recessed portions that are part of recess 332 and are configured to receive the intravascular device. In some embodiments, the recessed portions of the supports 342, 344, 346, and 348 include tapered surfaces similar to surfaces 334 and 336 discussed above. However, in other embodiments the recessed portions comprise only the bottom portion of the recess 332 that is sized and shaped to receive the intravascular device. It is understood that, in other embodiments, the arrangement of the recess 332 as defined by outer portions 338, 340 is similar to that defined by supports 342, 344, 346, and 348 and/or vice versa. In some embodiments, the spacings between the supports 342, 344, 346, and 348 are sized and shaped to allows the electrical contacts 314, 316, 318, 320, and 322 of the upper component 302 to move between the open and closed positions of the connector 300 as discussed below.

Referring again to FIGS. 35, 37, 39, 41, 45, and 47, to guide the movement of the upper component 302 with respect to the lower component 304, the openings 326 and 328 in the structure 324 of the upper component 302 receive projections or rods 350, 352 of the lower component 304. In that regard, as shown, the rods 350, 352 are sized and shaped to be slidably received within the openings 326, 328, respectively, such that the upper component 302 can translate along the length of the rods 350, 352. In some instances, the opposing ends of the rods 350, 352 include one or more structure features (e.g., projection, wall, etc.) to serve as a stop to limit the travel of the upper component 302 relative to the lower component 304. In some embodiments, the connector 300 includes a locking mechanism (e.g., projection and detent arrangement) to hold the connector in the closed position. Further, in some embodiments the connector 300 includes one or more bias elements (e.g., spring(s)) to urge the connector towards either the open or closed position.

To help ensure that the connection portion of the intravascular device is properly aligned with the electrical contacts of the connector 300, the upper and/or lower component(s) 302, 304 may include one or more visual markers (active and/or passive) as discussed above with respect to connectors 104, 170, and 200. Further, in the illustrated embodiment, the lower component 304 includes openings 354, 356, 358, 360, and 362 that extend through the lower surface of the lower component in general alignment with the electrical contacts 314, 316, 318, 320, and 322 of the upper component 302 and, therefore, in general alignment with where the conductive portions of the intravascular device should be positioned when received by the connector 300. Accordingly, in some instances a user can look through the opening to confirm proper positioning of the intravascular device within the connector 300, as shown in FIG. 36 for example. In that regard, when intravascular device 102 is utilized with connector 300, conductive portion 120 can be visualized through opening 354, conductive portion 122 can be visualized through at least one of openings 356 and 358, and conductive portion 124 can be visualized through at least one of openings 360 and 362. Also, the openings 354, 356, 358, 360, and 362 facilitate drainage of fluid out of the bottom of the connector 300.

Referring more specifically to FIGS. 44-47, shown therein is a transition of the connector 300 from the open positioned to the closed position. In that regard, the connector 300 is shown in the open position in FIGS. 44 and 45. As shown, the connector 300 is configured to receive the intravascular device 102 in a side-loading fashion. More specifically, the recess 332 in the lower component 304 is revealed when the upper component 302 is retracted to the open position such that the intravascular device 102 can be seated within the recess by moving the intravascular device 102 in a direction transverse to its longitudinal axis. To load the intravascular device 102 within the connector 300, the connector 300 may be moved relative to the intravascular device 102, the intravascular device 102 may be moved relative to the connector 300, and/or combinations thereof. With the intravascular device 102 positioned within the recess 332 of the lower component, the upper component 302 is translated with respect to the lower component 304 by sliding along rods 350, 352 to the closed position illustrated in FIGS. 46 and 47. In the closed position, the intravascular device 102 is held between the upper and lower components 302 and 304 such that the connector 300 is in electrical communication with the connection portion 114 of the intravascular device. In particular, as the upper component 302 is advanced towards the closed position the split teeth of the open-comb electrical contacts 314, 316, 318, 320, and 322 engage the connection portion 114 of the intravascular device 102. In that regard, the bottom of the recess 332 is positioned relative to the electrical contacts 314, 316, 318, 320, and 322 such that the intravascular device will be aligned with the electrical contacts 314, 316, 318, 320, and 322 in the vertical direction when the intravascular device is seated within the recess. Accordingly, with the intravascular device 102 seated in the recess such that the conductive portions 120, 122, and 124 of the connection portion 114 are aligned both horizontally and vertically with respect to the electrical contacts of the connector 300, advancement of the upper component 302 to the closed position electrically couples the connector 300 to the intravascular device 102.

Persons skilled in the art will also recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An intravascular system, comprising:
   an intravascular device comprising:
      a flexible elongate member having a proximal portion and a distal portion,
      at least one electronic component secured to the distal portion of the flexible elongate member, and
      at least one electrical connector secured to the proximal portion of the flexible elongate member, wherein the at least one electrical connector is electrically coupled to the at least one electronic component secured to the distal portion of the flexible elongate member; and
   a connector having at least one electrical contact configured to interface with the at least one electrical connector of the intravascular device, the connector including a first connection piece and a second connection piece, wherein the first connection piece is movable relative to the second connection piece between an open position and a closed position, wherein in the open position an elongated opening is formed between the first and second connection pieces to facilitate insertion of the at least one electrical connector between the first and second connection pieces in a direction transverse to a longitudinal axis of the intravascular device and wherein in the closed position the at least one electrical contact is electrically coupled to the at least one electrical connector received between the first and second connection pieces.

2. The system of claim 1, wherein the first connection piece is movable relative to the second piece about a pivot axis.

3. The system of claim 2, wherein a bias element urges the first and second connection pieces towards the closed position.

4. The system of claim 3, wherein the bias element is a spring.

5. The system of claim 2, wherein the second connection piece includes a recess sized and shaped to receive a portion of the intravascular device that includes the at least one electrical connector.

6. The system of claim 5, wherein the at least one electrical contact is secured to the first connection piece.

7. The system of claim 1, wherein the first piece includes at least one visual indicator for aligning the at least one electrical contact of the connector with the at least one electrical connector of the intravascular device.

8. The system of claim 7, wherein the at least one visual indicator comprises an arrow.

9. The system of claim 7, wherein the at least one visual indicator is a light.

10. The system of claim 9, wherein the light is configured to illuminate when a proper electrical coupling is achieved between the at least one electrical contact and the at least one electrical connector.

11. The system of claim 9, wherein the light is configured to illuminate a first color when a proper electrical coupling is achieved between the at least one electrical contact and the at least one electrical connector and configured to illuminate a second color when the proper electrical coupling between the at least one electrical contact and the at least one electrical connector is not achieved.

12. The system of claim 1, wherein the at least one electronic component is a pressure sensing component.

13. The system of claim 1, wherein the at least one electronic component is an intravascular imaging component.

14. The system of claim 13, wherein the intravascular imaging component includes at least one ultrasound transducer.

15. The system of claim 13, wherein the intravascular imaging component includes at least one optical coherence tomography (OCT) imaging element.

16. The system of claim 1, wherein the first connection piece is translatable relative to the second connection piece.

17. The system of claim 16, wherein the second connection piece includes at least one opening and the first connection piece includes at least one projection for movably engaging the at least one opening of the second connection piece such that the at least one opening guides translation of the first connection piece relative to the second connection piece.

18. The system of claim 17, wherein the at least one opening includes a first end and an opposing second end, and wherein the at least one projection is positioned adjacent the first end in the open position and is positioned adjacent the second end in the closed position.

19. The system of claim 16, wherein the second connection piece includes a recess sized and shaped to receive a portion of the intravascular device that includes the at least one electrical connector.

20. The system of claim 19, wherein the at least one electrical contact is secured to the first connection piece such that the at least one electrical contact is spaced from the recess of the second connection piece in the open position and extends across the recess of the second connection piece in the closed position.

21. The system of claim 5, wherein the recess extends from an opening on an end of the connector, wherein the connector further comprises a cable opening disposed on the end of the connector.

22. The system of claim 1, wherein the connector comprises a cable opening positioned such that a cable extends from the connector in a same direction as the intravascular device.

23. The system of claim 1, wherein the second connection piece comprises a recess, wherein the intravascular device is configured to be seated within the recess, and wherein the elongated opening is positioned relative to the first and second connection pieces to provide the intravascular device access to the recess.

* * * * *